United States Patent
Ajima

(10) Patent No.: US 10,357,198 B2
(45) Date of Patent: Jul. 23, 2019

(54) SYSTEM FOR ESTIMATING MUSCLE AREA, DEVICE, AND METHOD FOR ESTIMATING MUSCLE AREA

(71) Applicant: KYOCERA Corporation, Kyoto (JP)

(72) Inventor: Hiromi Ajima, Kawasaki (JP)

(73) Assignee: KYOCERA Corporation, Kyoto (JP)

(*) Notice: Subject to any disclaimer, the term of this patent is extended or adjusted under 35 U.S.C. 154(b) by 237 days.

(21) Appl. No.: 15/536,468

(22) PCT Filed: Dec. 9, 2015

(86) PCT No.: PCT/JP2015/006148
§ 371 (c)(1),
(2) Date: Jun. 15, 2017

(87) PCT Pub. No.: WO2016/103609
PCT Pub. Date: Jun. 30, 2016

(65) Prior Publication Data
US 2017/0332960 A1  Nov. 23, 2017

(30) Foreign Application Priority Data
Dec. 22, 2014  (JP) ................. 2014-258585

(51) Int. Cl.
*A61B 5/107* (2006.01)
*A61B 5/00* (2006.01)
(Continued)

(52) U.S. Cl.
CPC ............ *A61B 5/4519* (2013.01); *A61B 5/107* (2013.01); *A61B 5/1072* (2013.01);
(Continued)

(58) Field of Classification Search
CPC ....... A61B 5/107; A61B 5/102; A61B 5/1075; A61B 5/1077; A61B 5/4519; A61B 5/4869
See application file for complete search history.

(56) References Cited

U.S. PATENT DOCUMENTS

2002/0052697 A1* 5/2002 Serita ................... A61B 5/0537
702/30
2013/0301060 A1* 11/2013 Murakawa ........... A61B 5/0537
356/634
(Continued)

FOREIGN PATENT DOCUMENTS

| JP | 2001-212111 A | 8/2001 |
|---|---|---|
| JP | 2003-339658 A | 12/2003 |

(Continued)

OTHER PUBLICATIONS

Machine translation of Masuo. (Year: 2007).*
(Continued)

*Primary Examiner* — Thaddeus B Cox
(74) *Attorney, Agent, or Firm* — Studebaker & Brackett PC

(57) ABSTRACT

A system includes a measuring instrument including a first sensor that acquires orientation information of the measuring instrument and a device that obtains movement information of the measuring instrument, and a controller that estimates muscle area in a cross-section of a human body on the basis of shape characteristics calculated from an at least partial contour of the human body, the at least partial contour being calculated on the basis of the orientation information and the movement information.

11 Claims, 26 Drawing Sheets

(51) Int. Cl.
*G06T 1/00* (2006.01)
*A61B 6/03* (2006.01)
*A61B 6/00* (2006.01)
*G06T 7/00* (2017.01)
*G06T 7/60* (2017.01)

(52) U.S. Cl.
CPC .......... *A61B 5/1075* (2013.01); *A61B 5/1077* (2013.01); *A61B 5/6897* (2013.01); *A61B 6/032* (2013.01); *A61B 6/461* (2013.01); *A61B 6/5217* (2013.01); *G06T 1/00* (2013.01); *G06T 7/0012* (2013.01); *G06T 7/60* (2013.01); *G06T 2207/10081* (2013.01)

(56) References Cited

U.S. PATENT DOCUMENTS

| | | | |
|---|---|---|---|
| 2014/0121564 A1* | 5/2014 | Raskin | A61B 5/0022 600/587 |
| 2016/0242695 A1 | 8/2016 | Ajima | |
| 2016/0331276 A1* | 11/2016 | Shoshan | A61B 5/6898 |

FOREIGN PATENT DOCUMENTS

| | | | |
|---|---|---|---|
| JP | 2007-007445 A | | 1/2007 |
| JP | 2007014579 A | * | 1/2007 |
| JP | 2009-201670 A | | 9/2009 |
| JP | 2016-118953 A | | 6/2016 |
| WO | 2014/203539 A1 | | 12/2014 |

OTHER PUBLICATIONS

An Office Action; "Notice of Reasons for Rejection" issued by the Japanese Patent Office dated Sep. 5, 2017, which corresponds to Japanese Patent Application No. 2016-207861 and is related to U.S. Appl. No. 15/536,468; with English language Concise Explanation.
International Search Report issued in PCT/JP2015/006148; dated Mar. 8, 2016.
Written Opinion issued in PCT/JP2015/006148; dated Mar. 8, 2016; with English language Concise Explanation.

* cited by examiner

FIG. 8

| Record number | Time (s) | Orientation information (°) | Movement information (cm/sec²) | Movement amount (cm) |
|---|---|---|---|---|
| R0 | 0 | 0.00 | 0.00 | 0.00 |
| R1 | T1 | 2.05 | 0.85 | 0.42 |
| R2 | T2 | 3.10 | 1.52 | 1.40 |
| R3 | T3 | 5.81 | 2.65 | 3.25 |
| ⋮ | ⋮ | ⋮ | ⋮ | ⋮ |
| Rn | Tn | 360.00 | 0.00 | 82.05 |

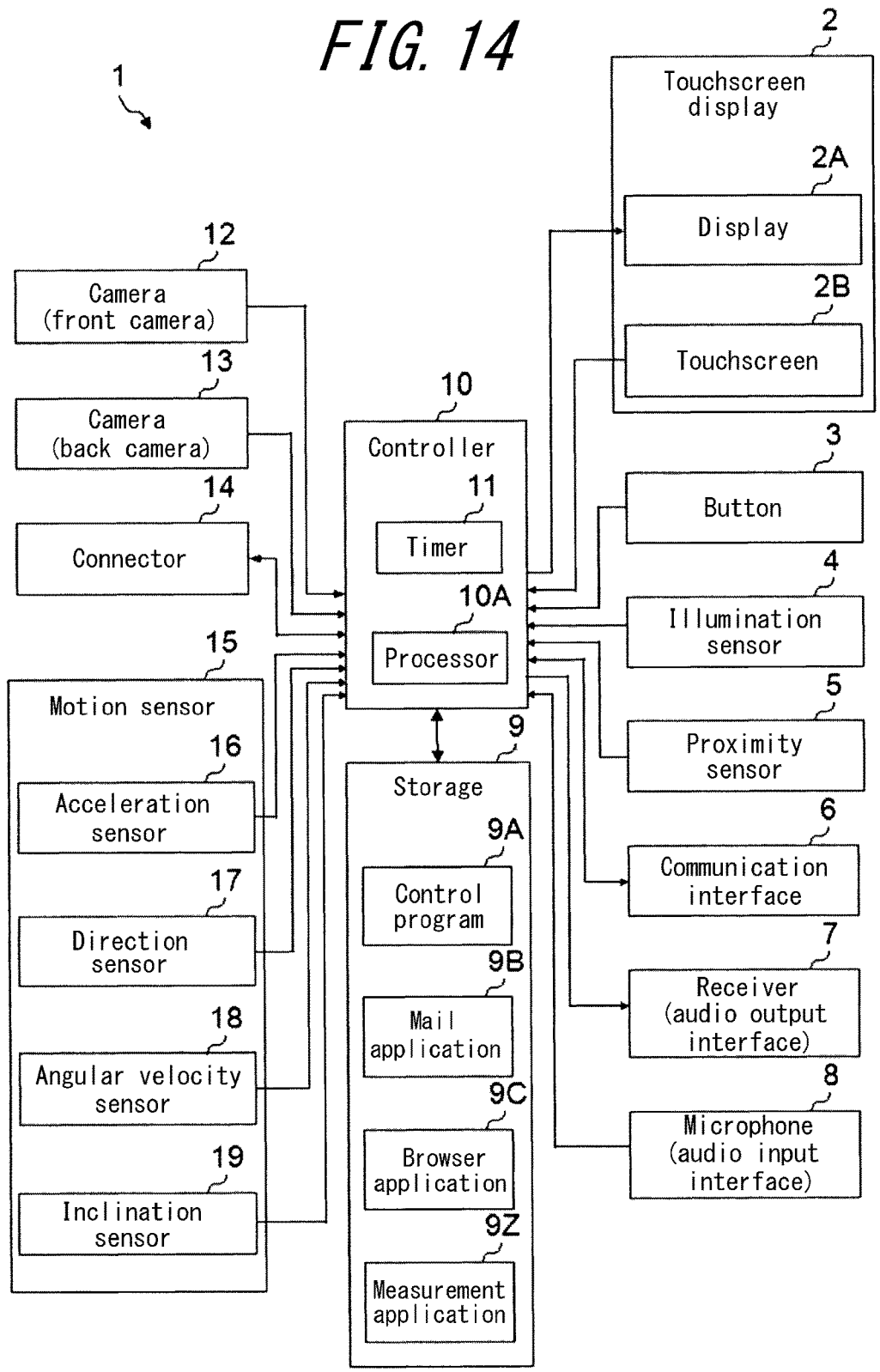

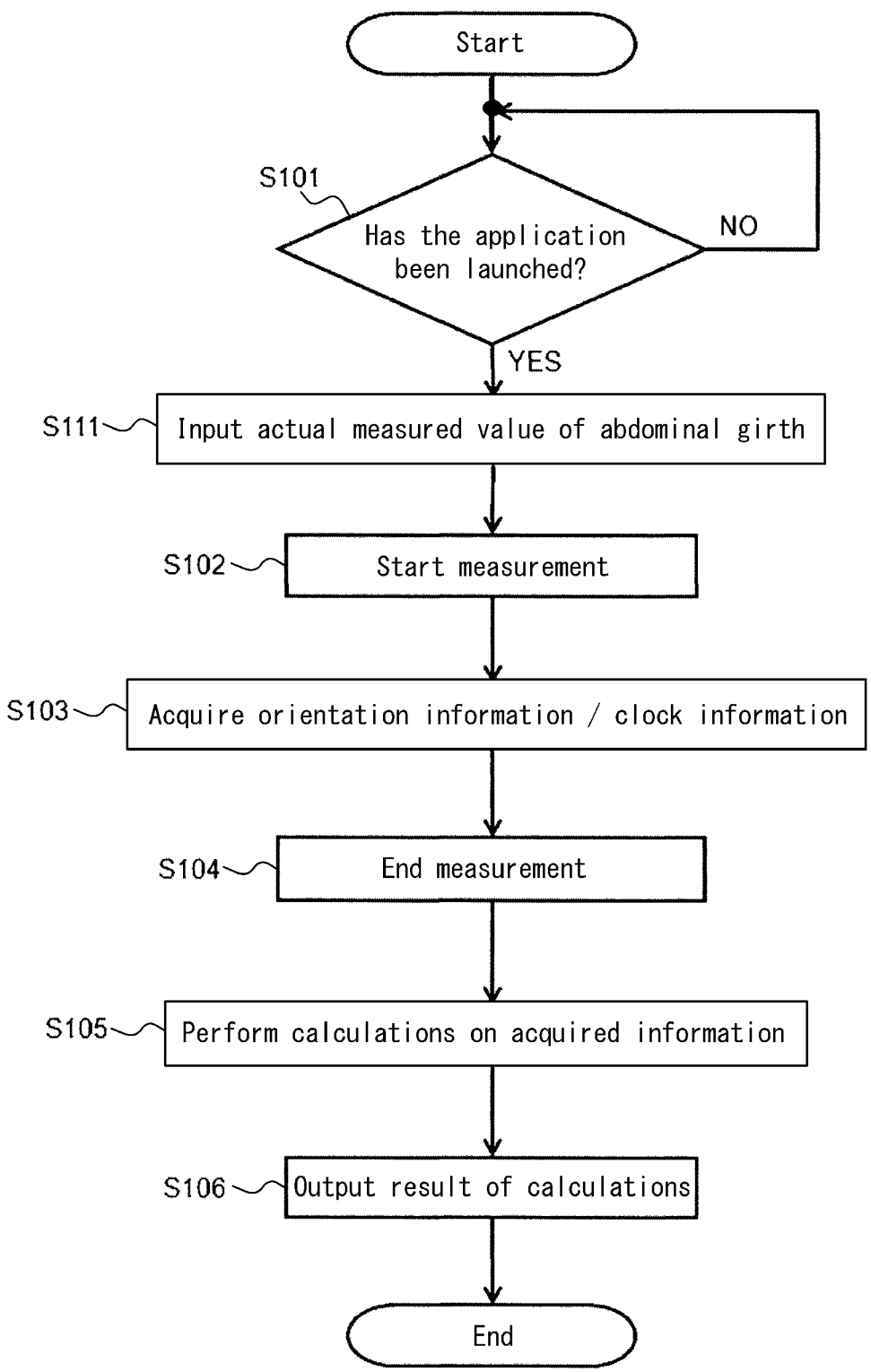

FIG. 16

| Record number | Time (s) | Orientation information (°) | Movement information (movement amount) (cm) |
|---|---|---|---|
| R0 | 0 | 0.00 | 0.00 |
| R1 | T1 | 1.01 | 0.41 |
| R2 | T2 | 1.50 | 0.82 |
| R3 | T3 | 0.51 | 1.23 |
| ⋮ | ⋮ | ⋮ | ⋮ |
| Rn | Tn | 360.00 | 82.05 |

| Record number | Time (s) | Orientation information (°/s) | Orientation (°) | Movement information (movement amount) |
|---|---|---|---|---|
| R0 | 0 | 0.00 | 0.00 | 0.00 |
| R1 | T1 | 8.22 | 1.37 | 0.42 |
| ⋮ | ⋮ | ⋮ | ⋮ | ⋮ |
| R(n/4) | T(n/4) | 48.72 | 90 | 20.50 |
| ⋮ | ⋮ | ⋮ | ⋮ | ⋮ |
| R(n/2) | T(n/2) | 0.44 | 180 | 41.00 |
| ⋮ | ⋮ | ⋮ | ⋮ | ⋮ |
| R(n') | T(n') | 38.21 | 190.12 | 43.15 |

*FIG. 21*

|  |  | Abdominal girth (cm) | | | | |
|---|---|---|---|---|---|---|
|  |  | ~70 | 71~80 | 81~90 | 91~100 | 101~ |
| Muscle area A (cm²) | ~50 | P11 | P12 | P13 | P14 | P15 |
| | 51~100 | P21 | P22 | P23 | P24 | P25 |
| | 101~150 | P31 | P32 | P33 | P34 | P35 |
| | 151~200 | P41 | P42 | P43 | P44 | P45 |
| | 201~ | P51 | P52 | P53 | P54 | P55 |

SYSTEM FOR ESTIMATING MUSCLE AREA, DEVICE, AND METHOD FOR ESTIMATING MUSCLE AREA

CROSS-REFERENCE TO RELATED APPLICATION

This application claims priority to and the benefit of Japanese Patent Application No. 2014-258585 filed Dec. 22, 2014, the entire contents of which are incorporated herein by reference.

TECHNICAL FIELD

This disclosure relates to a system for estimating muscle area, a device, and a method for estimating muscle area.

BACKGROUND

Methods are known for calculating muscle area from a cross-sectional image obtained by computed tomography (CT). Methods for measuring muscle mass using a bioimpedance method are also known.

SUMMARY

A system for estimating muscle area according to this disclosure includes: a measuring instrument including a first sensor configured to acquire orientation information of the measuring instrument and a device configured to obtain movement information of the measuring instrument; and a controller configured to estimate muscle area in a cross-section of a human body on a basis of shape characteristics calculated from an at least partial contour of the human body, the at least partial contour being calculated on a basis of the orientation information and the movement information.

An apparatus according to this disclosure includes a first sensor configured to acquire orientation information of the apparatus; a device configured to obtain movement information of the apparatus; and a controller configured to estimate muscle area in a cross-section of a human body on a basis of shape characteristics calculated from an at least partial contour of the human body, the at least partial contour being calculated on a basis of the orientation information and the movement information.

A method for estimating muscle area according to this disclosure includes: obtaining orientation information and movement information of an apparatus; and with a controller, calculating an at least partial contour of a human body on a basis of the orientation information and the movement information; calculating shape characteristics from the calculated at least partial contour of the human body; and estimating muscle area in a cross-section of a human body on a basis of the shape characteristics.

BRIEF DESCRIPTION OF THE DRAWINGS

In the accompanying drawings:

FIG. 8 is an example of a record of orientation information and movement information according to Embodiment 1;

FIG. 14 is a schematic block diagram illustrating the functions of a smartphone according to Embodiment 2;

FIG. 15 is a flowchart for measurement of a contour of a cross-section according to Embodiment 2;

FIG. 16 is an example of a record of orientation information and movement information according to Embodiment 2;

FIG. 21 is an example of a classification table of abdominal cross-sectional images according to Embodiment 3;

DETAILED DESCRIPTION

Few facilities are equipped to perform measurement using CT or the bioimpedance method. It would be helpful to provide a system for estimating muscle area, a device, and a method for estimating muscle area that can estimate muscle area with a simple technique.

Embodiments of this disclosure are described below in detail with reference to the accompanying drawings.

In the embodiments, a smartphone 1 is adopted as an example of an apparatus, and the case of estimating the muscle area of a person's abdomen and thigh is described.

Embodiment 1

The smartphone 1 is an apparatus that includes a first sensor that obtains orientation information, a device that obtains movement information, and a controller 10 that calculates the contour of a cross-section of a measured part. In this embodiment, the device that obtains movement information includes a second sensor.

Figure 1:
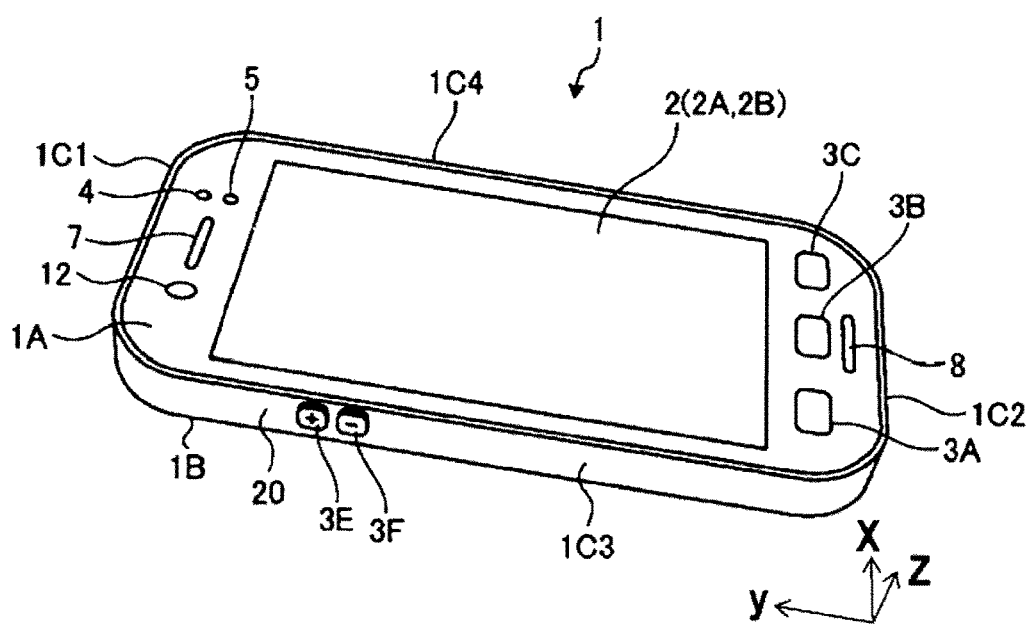
FIG. 1 is a schematic perspective view illustrating the appearance of a smartphone according to Embodiment 1.
Figure 2:
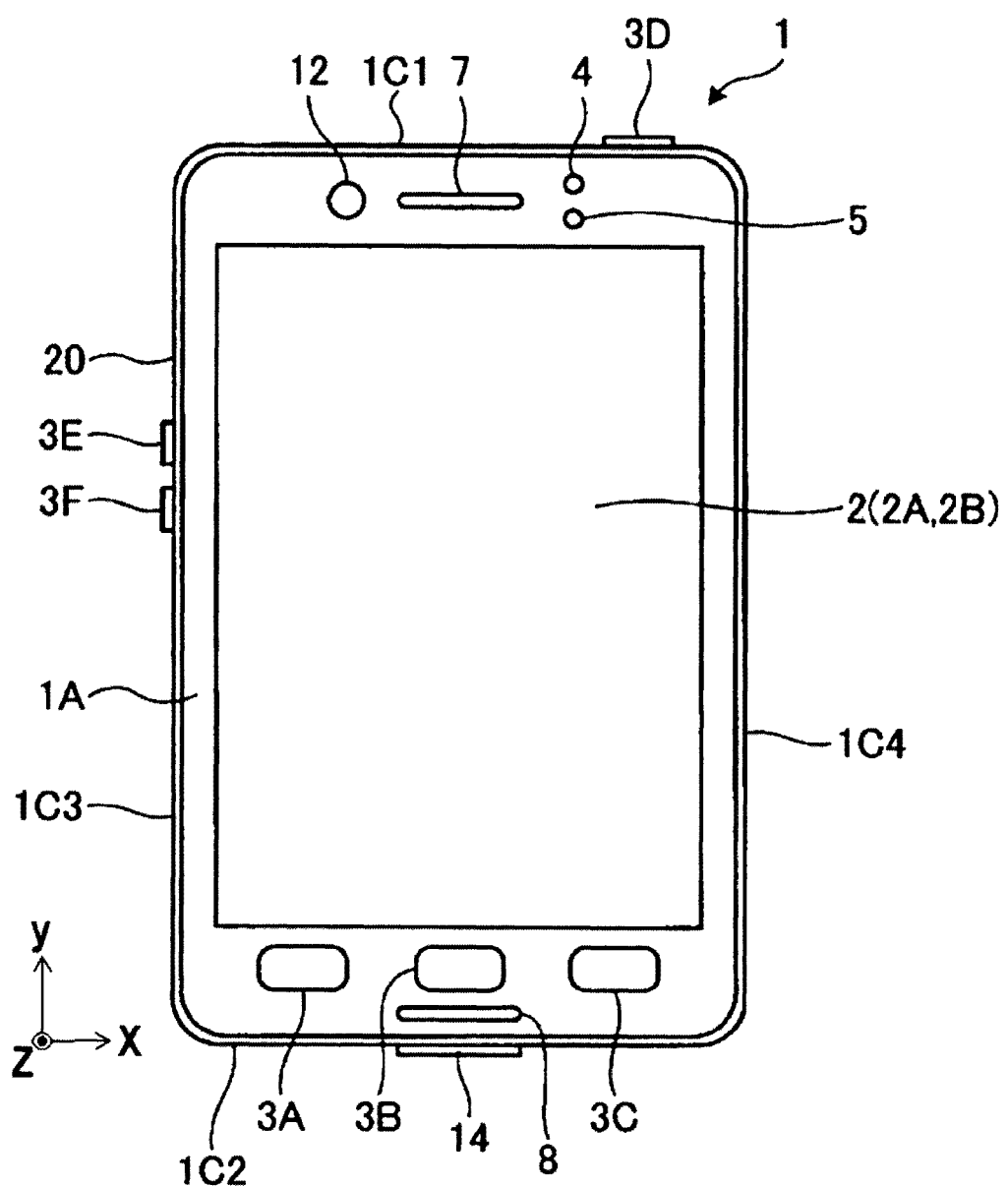
FIG. 2 is a schematic front view illustrating the appearance of the smartphone according to Embodiment 1.
Figure 3:
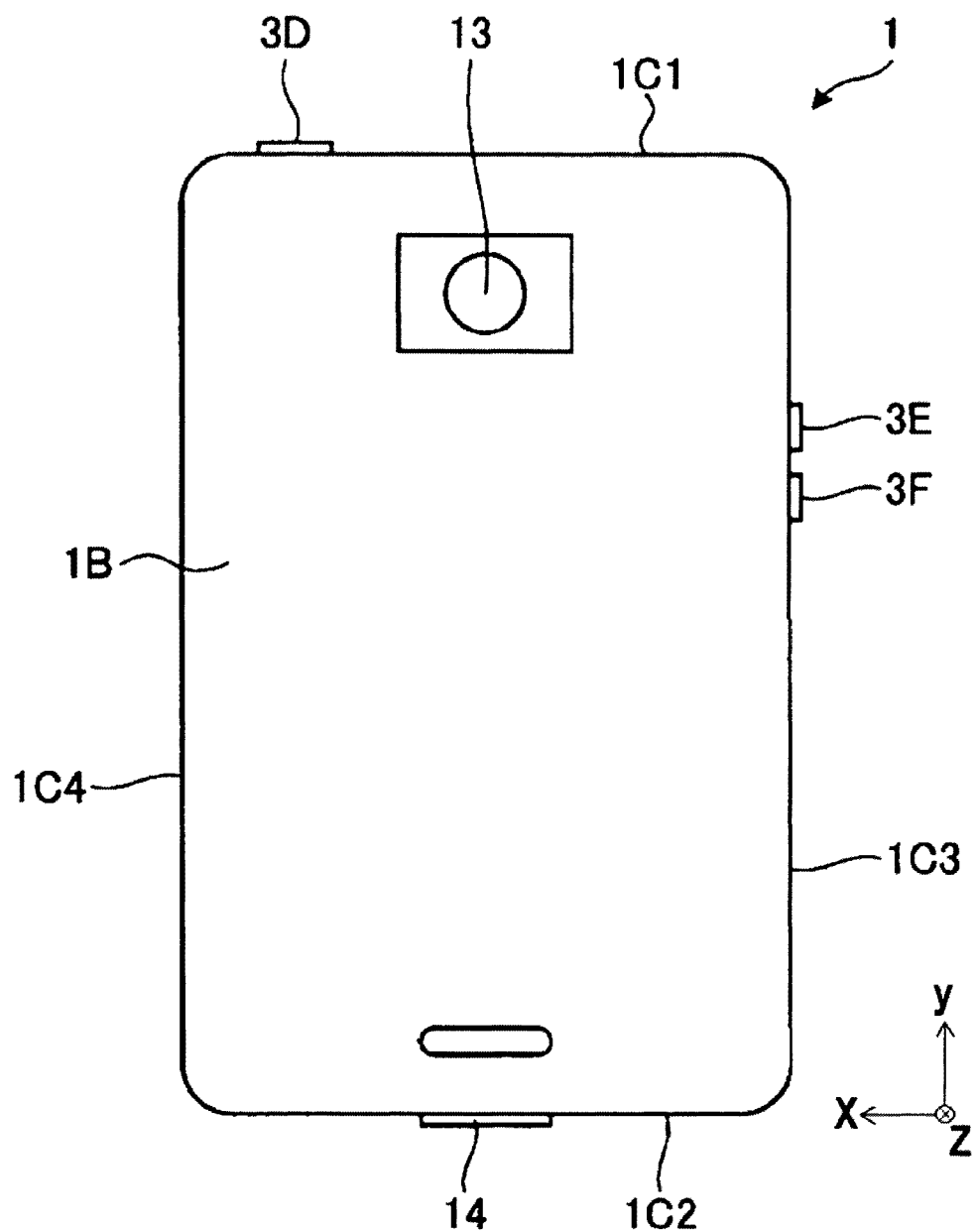
FIG. 3 is a schematic back view illustrating the appearance of the smartphone according to Embodiment 1.

The appearance of the smartphone 1 according to Embodiment 1 is described with reference to FIGS. 1 to 3.

A housing 20 includes a front face 1A, a back face 1B, and side faces 1C1 to 1C4. The front face 1A is the front surface of the housing 20. The back face 1B is the back surface of the housing 20. The side faces 1C1 to 1C4 are side surfaces that connect the front face 1A and the back face 1B. The side faces 1C1 to 1C4 may be collectively referred to below as the side faces 1C without further distinction.

On the front face 1A, the smartphone 1 includes a touchscreen display 2, buttons 3A to 3C, an illumination sensor 4, a proximity sensor 5, a receiver 7, a microphone 8, and a front camera 12. The smartphone 1 includes a back camera 13 on the back face 1B. The smartphone 1 also includes buttons 3D to 3F and a connector 14 on the side faces 1C. The buttons 3A to 3F may be collectively referred to below as the buttons 3 without further distinction.

The touchscreen display 2 includes a display 2A and a touchscreen 2B. The display 2A is provided with a display device such as a liquid crystal display, an organic electro-luminescence panel, or an inorganic electro-luminescence panel. The display 2A displays information such as letters, images, symbols, and graphics.

The touchscreen 2B detects contact on the touchscreen 2B by a finger, stylus pen, or other such object. The touchscreen 2B can detect the position at which a plurality of fingers, a stylus pen, or another object contacts the touchscreen 2B.

Any detection system may be used in the touchscreen 2B, such as a capacitive system, a resistive film system, a surface acoustic wave system (or an ultrasonic wave system), an infrared system, an electromagnetic induction system, or a load detection system. In a capacitive system, contact and proximity of an object such as a finger or stylus pen can be detected.

Figure 4:
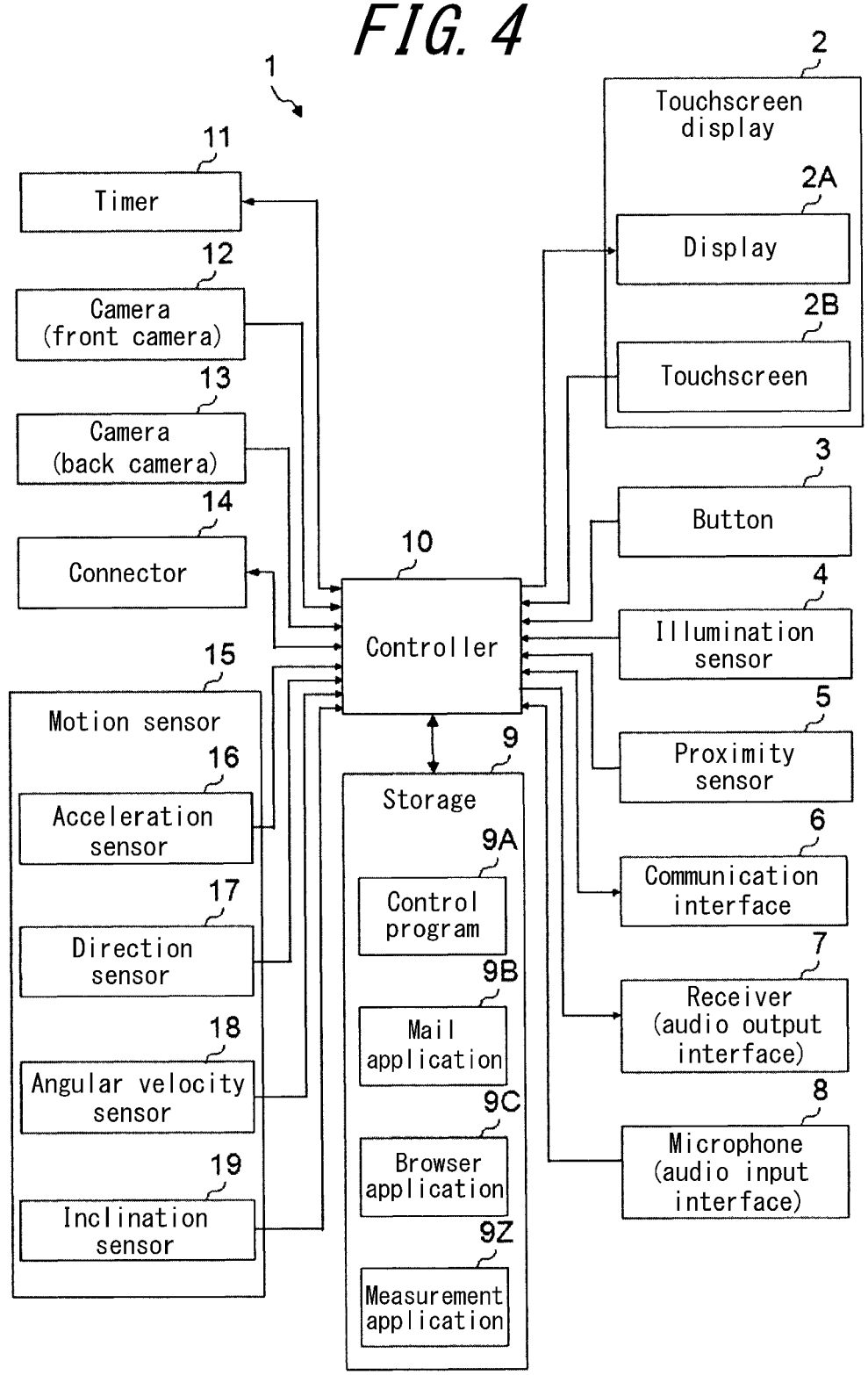
FIG. 4 is a schematic block diagram illustrating the functions of the smartphone according to Embodiment 1.

FIG. 4 is a block diagram illustrating the configuration of the smartphone 1. The smartphone 1 includes a touchscreen display 2, buttons 3, an illumination sensor 4, a proximity sensor 5, a communication interface 6, a receiver 7, a microphone 8, a storage 9, a controller 10, a timer 11, a front camera 12, a back camera 13, a connector 14, and a motion sensor 15.

As described above, the touchscreen display 2 includes a display 2A and a touchscreen 2B. The display 2A displays information such as letters, images, symbols, and graphics. The touchscreen 2B receives input of contact on a receiving area. In other words, the touchscreen 2B detects contact. The controller 10 detects a gesture on the smartphone 1. The controller 10 cooperates with the touchscreen 2B to detect an operation (gesture) on the touchscreen 2B (touchscreen display 2). The controller 10 also cooperates with the touchscreen 2B to detect an operation (gesture) on the display 2A (touchscreen display 2).

The buttons 3 are operated by the user. The buttons 3 include button 3A to button 3F. The controller 10 cooperates with the buttons 3 to detect an operation on the buttons. Examples of operations on the buttons include a click, a double-click, a push, a long push, and a multi-push.

For example, the buttons 3A to 3C may be a home button, a back button, or a menu button. In this embodiment, touch-sensor buttons are used as the buttons 3A to 3C. The button 3D may, for example, be a power button for the smartphone 1. The button 3D may also function as a button to engage/release a sleep mode. The buttons 3E and 3F may, for example, be volume buttons.

The illumination sensor 4 detects the degree of illumination. The degree of illumination may, for example, be the intensity of light, brightness, or luminance. The illumination sensor 4 may, for example, be used to adjust the luminance of the display 2A.

The proximity sensor 5 detects the presence of a nearby object without contact. The proximity sensor 5 may, for example, detect that the touchscreen display 2 has been brought close to a face.

The communication interface 6 communicates wirelessly. The communication method of the communication interface 6 is prescribed by a wireless communication standard. For example, a cellular phone communication standard such as 2G, 3G, or 4G may be used as the wireless communication standard. Examples of cellular phone communication standards include Long Term Evolution (LTE), W-CDMA, CDMA2000, PDC, Global System for Mobile communications (GSM®) (GSM is a registered trademark in Japan, other countries, or both)), and Personal Handy-phone System (PHS). Examples of wireless communication standards include Worldwide Interoperability for Microwave Access (WiMAX), IEEE802.11, Bluetooth® (Bluetooth is a registered trademark in Japan, other countries, or both), IrDA, and NFC. The communication interface 6 may support one or more of the aforementioned communication standards.

The receiver 7 outputs an audio signal, transmitted from the controller 10, as sound. The microphone 8 converts sound from the user or another source to an audio signal and transmits the audio signal to the controller 10. The smartphone 1 may include a speaker instead of the receiver 7.

The storage 9 stores programs and data. The storage 9 may also be used as a working area to store results of processing by the controller 10 temporarily. The storage 9 may include any storage device, such as a semiconductor storage device or a magnetic storage device. The storage 9 may also include a plurality of types of storage devices. The storage 9 may include a combination of a portable storage medium, such as a memory card, and an apparatus for reading the storage medium.

The programs stored on the storage 9 include applications that run in the foreground or the background and a control program that supports operations of the application. The applications may, for example, display a predetermined screen on the display 2A and cause the controller 10 to execute processing in accordance with a gesture detected by the touchscreen 2B. The control program may, for example, be an OS. The applications and the control program may be installed on the storage 9 through wireless communication by the communication interface 6 or from a storage medium.

The storage 9 for example stores a control program 9A, a mail application 9B, a browser application 9C, and a measurement application 9Z. The mail application 9B provides e-mail functions for actions such as creating, sending, receiving, and displaying e-mail. The browser application 9C provides a Web browsing function to display Web pages. The measurement application 9Z provides a function for the user of the smartphone 1 to measure the contour of a cross-section of a measured part.

The control program 9A provides functions related to various types of control for running the smartphone 1. The control program 9A may, for example, implement a phone call by controlling the components such as the communication interface 6, receiver 7, and microphone 8. The functions provided by the control program 9A may be used in combination with functions provided by other programs, such as the mail application 9B.

The controller 10 may, for example, be a Central Processing Unit (CPU). The controller 10 may be a System-on-a-Chip (SoC) or other type of integrated circuit in which other components, such as the communication interface 6, are integrated. The controller 10 may be configured by combining a plurality of integrated circuits. The controller 10 implements a variety of functions by comprehensively controlling operations of the smartphone 1.

In greater detail, while referring as necessary to data stored in the storage 9, the controller 10 executes commands included in the programs stored in the storage 9 to control components such as the display 2A, the communication interface 6, and the motion sensor 15, thereby implementing various functions. The controller 10 implements various functions by executing commands included in the measurement application 9Z stored in the storage 9. The controller 10 can change the control in response to detection results from various detectors, such as the touchscreen 2B, buttons 3, and motion sensor 15. In this embodiment, the entire controller 10 functions as a control unit. The controller 10 calculates a contour of a cross-section of a measured part on the basis of orientation information acquired by the first sensor and movement information acquired by the second sensor.

The timer 11 outputs a clock signal with a preset frequency. The timer 11 receives an instruction for a timer operation from the controller 10 and outputs the clock signal to the controller 10. The first sensor and the second sensor acquire orientation information and movement information multiple times in accordance with clock signals input through the controller 10. The timer 11 may be provided external to the controller 10 or may be included in the controller 10, as illustrated below in FIG. 14.

The front camera 12 captures an object facing the front face 1A. The back camera 13 captures an object facing the back face 1B.

The connector 14 is a terminal to which another apparatus connects. The connector 14 of this embodiment also functions as a communication interface for communication between the smartphone 1 and another apparatus over a connection object connected to the terminal. The connector 14 may be a general-purpose terminal such as a Universal Serial Bus (USB), High-Definition Multimedia Interface (HDMI® (HDMI is a registered trademark in Japan, other countries, or both)), Mobile High-definition Link (MHL), Light Peak, Thunderbolt, Local Area Network connector, or an earphone microphone connector. The connector 14 may be designed as a dedicated terminal, such as a Dock connector. Examples of the apparatuses that connect to the connector 14 include a charger, an external storage, a speaker, a communication apparatus, and an information processing apparatus.

The motion sensor 15 detects a motion factor. This motion factor is mainly processed as a control factor of the smartphone 1, which is the apparatus. The control factor is a factor indicating the circumstances of the apparatus and is processed by the controller 10. The motion sensor 15 of this embodiment includes an acceleration sensor 16, a direction sensor 17, an angular velocity sensor 18, and an inclination sensor 19. The combined output of the acceleration sensor 16, direction sensor 17, angular velocity sensor 18, and inclination sensor 19 can be used. By processing the combined output of the motion sensor 15, the controller 10 can execute processing that amply reflects the movement of the smartphone 1, which is the apparatus.

In this embodiment, the first sensor obtains the orientation information of the smartphone 1, which is the apparatus. The orientation information of the smartphone is output from the first sensor. The orientation information of the smartphone 1 is related to the direction in which the smartphone 1 is facing. The orientation information of the smartphone 1 for example includes the direction of the earth's magnetism, the inclination relative to the earth's magnetism, the direction of the rotation angle, the change in the rotation angle, the direction of gravity, and the inclination relative to the direction of gravity.

The orientation of the smartphone 1 refers to the direction of a normal to the surface of the housing 20 that is opposite a measured part when the contour of a cross-section of the measured part is being measured. The surface of the housing 20 that is opposite the measured part may be any surface whose orientation can be detected by the first sensor. This surface may be any of the front face 1A, the back face 1B, and the side faces 1C1 to 1C4.

In this embodiment, the direction sensor 17 is used in the first sensor. The direction sensor 17 is a sensor that detects the orientation of the earth's magnetism. In this embodiment, the component when the orientation of the smartphone 1 is projected onto a plane parallel to the ground is the orientation information acquired by the direction sensor 17. The orientation information acquired by the direction sensor 17 is the direction of the smartphone 1. The direction of the smartphone 1 can be acquired as 0° to 360° orientation information. For example, the orientation information that is acquired is 0° when the smartphone 1 is facing north, 90° when facing east, 180° when facing south, and 270° when facing west. In this embodiment, the direction sensor 17 can more accurately acquire the orientation information as a result of a cross-section of the measured part being parallel to the ground. Since the measured part is the abdomen in this embodiment, measurement may be made while the user is standing.

The direction sensor 17 outputs the detected orientation of the earth's magnetism. For example, when the orientation of the earth's magnetism is output as a motion factor, the controller 10 can execute processing using this motion factor as a control factor that reflects the direction in which the smartphone 1 faces. For example, when the change in the orientation of the earth's magnetism is output as a motion factor, the controller 10 can execute processing using this motion factor as a control factor that reflects the change in the orientation of the smartphone 1.

The angular velocity sensor 18 may be used in the first sensor. The angular velocity sensor 18 detects the angular velocity of the smartphone 1. The angular velocity sensor 18 can acquire the angular velocity of the smartphone 1 as orientation information. The controller 10 calculates the orientation of the smartphone 1 by time integrating the acquired angular velocity once. The calculated orientation of the smartphone 1 is an angle relative to an initial value at the start of measurement.

The angular velocity sensor 18 outputs the detected angular velocity. For example, when the orientation of the angular velocity is output as a motion factor, the controller 10 can execute processing using this motion factor as a control factor that reflects the rotation direction of the smartphone 1. For example, when the magnitude of the angular velocity is output, the controller 10 can execute processing using this magnitude as a control factor that reflects the rotation amount of the smartphone 1.

The inclination sensor 19 may also be used in the first sensor. The inclination sensor 19 detects the gravitational acceleration acting on the smartphone 1. The inclination sensor 19 can acquire the gravitational acceleration of the smartphone 1 as orientation information. For example, with the inclination sensor 19, the smartphone 1 can acquire −9.8 m/s$^2$ to 9.8 m/s$^2$ as the orientation information. The acquired orientation information is 9.8 m/s$^2$ when, for example, the y-axis direction of the smartphone 1 illustrated in FIG. 1 is the same as the direction of gravity and is −9.8 m/s$^2$ in the opposite case. When the y-axis direction is perpendicular to the direction of gravity, the acquired orientation information is 0 m/s$^2$. In this embodiment, the inclination sensor 19 can more accurately acquire the orientation information as a result of a cross-section of the measured part being perpendicular to the ground. When the measured part is the abdomen, measurement may be performed while the user is lying down.

The inclination sensor 19 outputs the detected inclination. For example, when the inclination relative to the direction of gravity is output as a motion factor, the controller 10 can execute processing using this motion factor as a control factor that reflects the inclination of the smartphone 1.

In some cases, the controller 10 calculates the orientation on the basis of the orientation information of the smartphone 1. For example, the above-described angular velocity sensor 18 acquires the angular velocity as orientation information. On the basis of the acquired angular velocity, the controller 10 calculates the orientation of the smartphone 1. As another example, the above-described inclination sensor 19 acquires the gravitational acceleration as orientation information. On the basis of the acquired gravitational acceleration, the controller 10 calculates the orientation of the smartphone 1 relative to the direction of gravity.

The first sensor can use a combination of the above-described motion sensors. By processing a combination of orientation information from a plurality of motion sensors, the controller 10 can more accurately calculate the orientation of the smartphone 1, which is the apparatus.

In this embodiment, the device for obtaining movement information of the apparatus is the second sensor. The second sensor obtains movement information of the smartphone 1, which is the apparatus. The movement information of the smartphone 1 is output from the second sensor. The movement information of the smartphone 1 is related to the movement amount of the smartphone 1. The movement information of the smartphone 1 for example includes acceleration, speed, and movement amount.

In this embodiment, the movement amount of the smartphone 1 is the movement amount of a reference position of the housing 20 in the smartphone 1. The reference position of the housing 20 may be any position detectable by the second sensor, such as the surface of the side face 1C1.

In this embodiment, the acceleration sensor 16 is used in the second sensor. The acceleration sensor 16 detects the acceleration acting on the smartphone 1. The acceleration sensor 16 can acquire the acceleration of the smartphone 1 as movement information. The controller 10 calculates the movement amount of the smartphone 1 by time integrating the acquired acceleration twice.

The acceleration sensor 16 outputs the detected acceleration. For example, when the direction of the acceleration is output, the controller 10 can execute processing using this direction as a control factor that reflects the direction in which the smartphone 1 is moving. For example, when the magnitude of the acceleration is output, the controller 10 can execute processing using this magnitude as a control factor that reflects the speed at which the smartphone 1 is moving and the movement amount.

The controller 10 calculates the contour of a cross-section of the measured part. The contour of a cross-section of the measured part is calculated on the basis of the orientation information and movement information acquired by the first sensor and the second sensor. In some cases, the controller 10 calculates the orientation and the movement amount during the calculation process.

A sensor that can detect motion factors in three axial directions is used in the above-described motion sensor 15. The three axial directions detected by the motion sensor 15 of this embodiment are approximately orthogonal to each other. The x-direction, y-direction, and z-direction illustrated in FIGS. 1 to 3 correspond to the three axial directions of the motion sensor 15. The three axial directions need not be orthogonal to each other. In a motion sensor 15 in which the three directions are not orthogonal to each other, motion factors in three orthogonal directions can be calculated. The direction serving as a reference may differ for each motion sensor 15. In this embodiment, each motion sensor is not necessarily a three-axis sensor. The controller 10 can calculate the contour of a cross-section with the orientation information in one axial direction and the movement information in one axial direction.

The first sensor and the second sensor may use any of the above-described motion sensors 15 or another motion sensor.

A portion or all of the program that is stored in the storage 9 in FIG. 4 may be downloaded by the communication interface 6 from another apparatus by wireless communication. Also, a portion or all of the program that is stored in the storage 9 in FIG. 4 may be stored in a storage medium that is readable by a reading apparatus included in the storage 9. A portion or all of the program that is stored in the storage 9 in FIG. 4 may also be stored in a flash memory, Hard Disc Drive (HDD), Compact Disc (CD), Digital Versatile Disc (DVD®), or Blu-ray® Disc (BD) (DVD and Blu-ray are registered trademarks in Japan, other countries, or both) that is readable by a reading apparatus that connects to the connector 14.

The configuration of the smartphone 1 illustrated in FIGS. 1 to 4 is only an example and may be changed as necessary without departing from the scope of this disclosure. For example, the number and type of buttons 3 are not limited to the example in FIG. 1. Instead of including the buttons 3A to 3C, for example, the smartphone 1 may include buttons arranged as a numeric keypad, a QWERTY keyboard, or another arrangement as buttons for operating the screen. In order to operate the screen, the smartphone 1 may include just one button or may lack buttons altogether. In the example in FIG. 4, the smartphone 1 includes two cameras, but the smartphone 1 may include just one camera or may lack cameras altogether. The illumination sensor 4 and the proximity sensor 5 may be configured by one sensor. In the example illustrated in FIG. 4, four types of sensors are provided to acquire the orientation information and the movement information of the smartphone 1, which is the apparatus. The smartphone 1 need not include all of these sensors, however, and may include other types of sensors.

Figure 5:
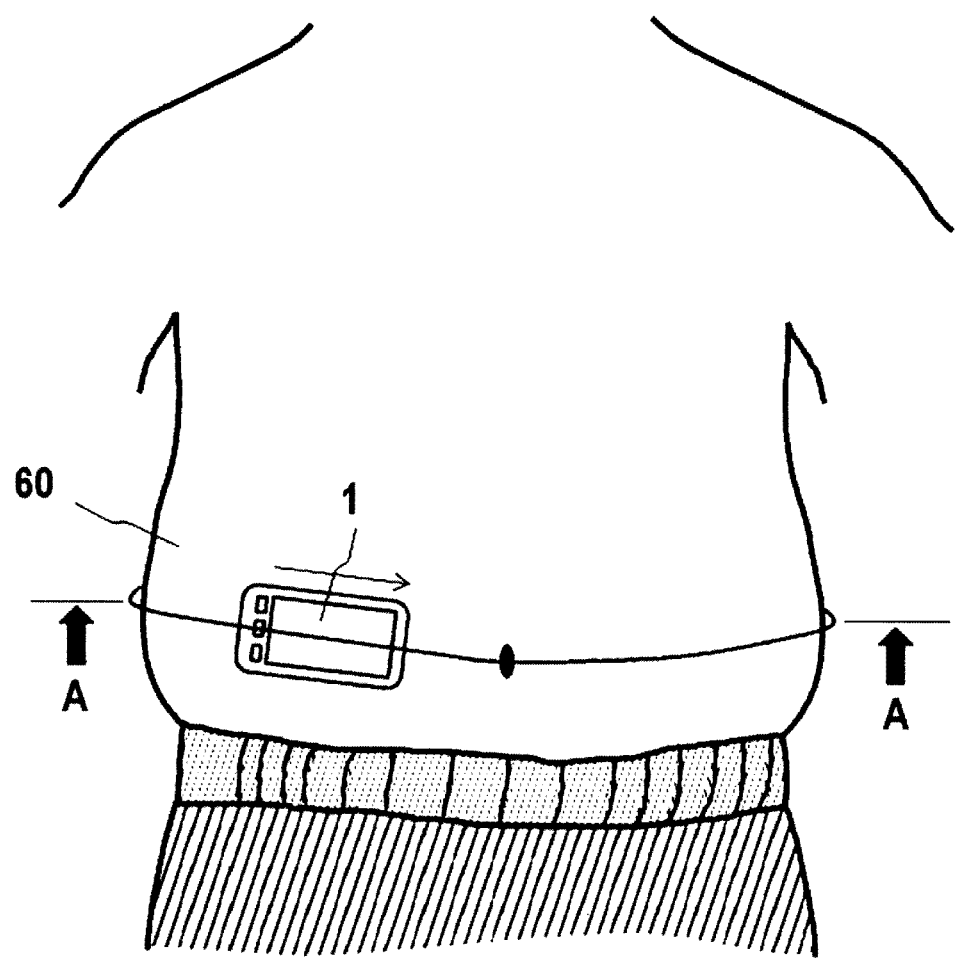
FIG. 5 is a schematic diagram illustrating measurement of the contour of an abdominal cross-section according to Embodiment 1.
Figure 6:
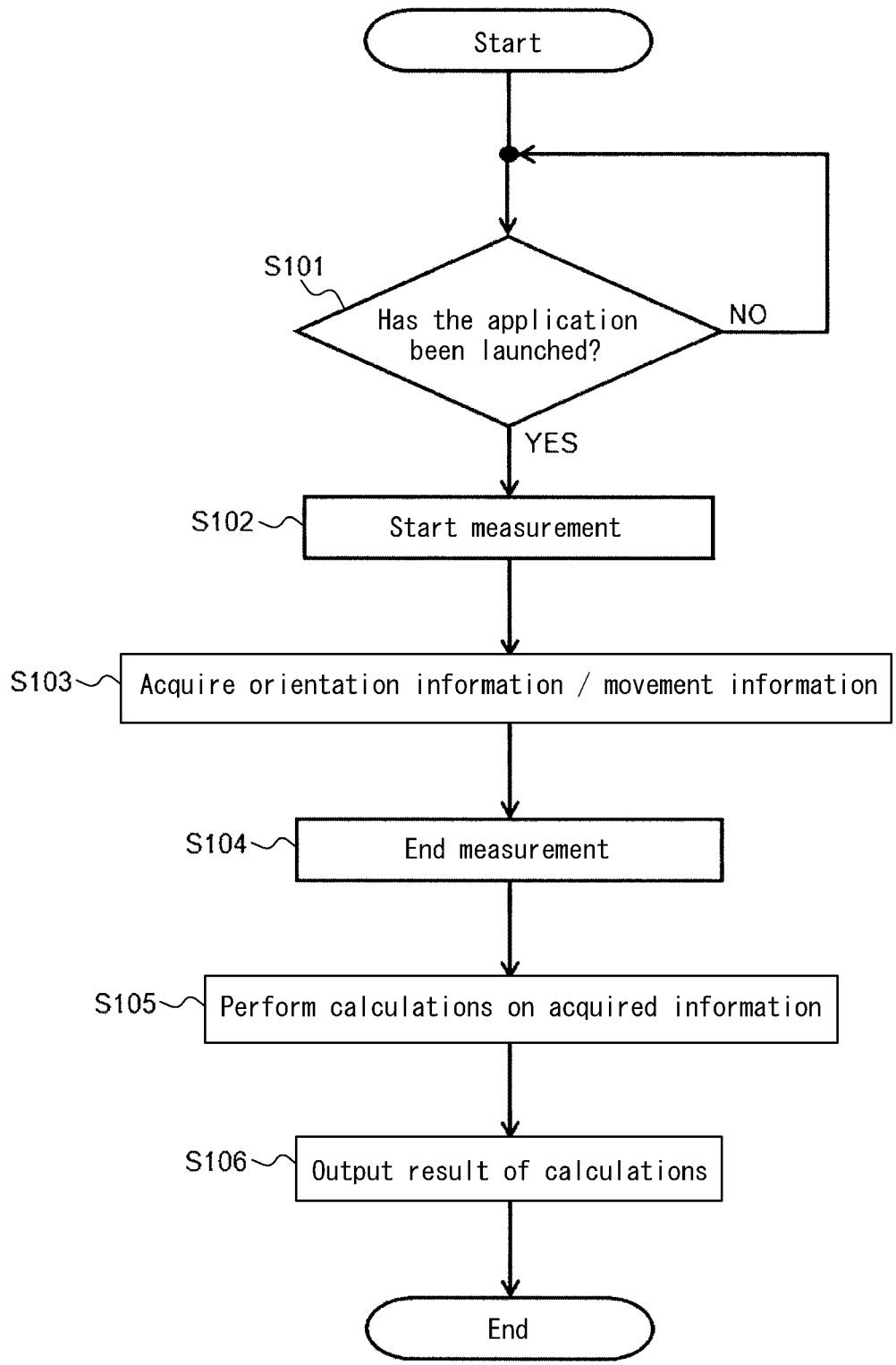
FIG. 6 is a flowchart for measurement of a contour of a cross-section according to this disclosure.

Next, with reference to FIGS. 5 and 6, measurement of the contour of an abdominal cross-section by the smartphone 1 according to Embodiment 1 is described.

FIG. 5 is a schematic diagram illustrating measurement of the contour of an abdominal cross-section according to Embodiment 1.

FIG. 6 is a flowchart for measurement of the contour of an abdominal cross-section according to Embodiment 1.

In step S101, the user launches the measurement application 9Z for measuring the contour of a cross-section. Next, measurement begins in step S102. At the start of measurement, the smartphone 1 is placed against the surface of the abdomen 60 at any position where the contour of a cross-section of the abdomen is to be measured. In this embodiment, the contour of a cross-section at the height of the user's navel (the position indicated by A-A in FIG. 5) is measured. As long as measurement of the contour of the cross-section is not impeded, the smartphone 1 may be contacted to the surface of the abdomen 60 directly or with clothing therebetween. The measurement start position may be anywhere along the abdominal A-A position. To start measurement, the user performs a preset start action on the smartphone 1. The start action set in advance may be an action such as pushing one of the buttons 3 of the smartphone 1 or tapping a particular position on the touchscreen 2B. The surface that opposes the abdominal surface may be any of the front face 1A, back face 1B, and side faces 1C1 to 1C4 of the smartphone 1. For operability, however, the back face 1B is the opposing face in this embodiment.

In step S103, the user moves the smartphone 1 along the surface at the A-A position of the abdomen 60 once around the abdomen 60. If the user moves the smartphone 1 at a constant speed while keeping the smartphone 1 against the surface of the abdomen 60, the interval between acquisition of various information becomes constant, which increases the accuracy of contour measurement.

In step S103, under conditions programmed in advance, the direction sensor 17 acquires orientation information and the acceleration sensor 16 acquires movement information. The orientation information and movement information are acquired multiple times. The orientation information and the movement information are acquired in accordance with the clock signal output from the timer 11. The acquisition cycle for each type of information may be selected in accordance with the size and complexity of the cross-section of the measured part. The acquisition cycle of information may, for example, be selected from among a sampling frequency of 5 Hertz (Hz) to 60 Hz. The acquired orientation information and movement information are temporarily stored inside the smartphone 1. This measurement is continuously made from the start of step S102 until the end of step S104.

After moving the smartphone 1 once around the abdomen 60 while keeping the smartphone 1 against the abdomen 60, the user performs an end action, set in advance, on the smartphone 1 to end measurement (step S104). The end action set in advance may be an action such as pushing one of the buttons 3 of the smartphone 1 or tapping a particular position on the touchscreen 2B. Alternatively, the smartphone 1 may automatically end measurement by recognizing one circumference when the orientation information acquired by the direction sensor 17 of the smartphone 1 matches the orientation information at the start of measurement or changes by 360° from the orientation information at the start of measurement. In the case of automatic recognition, the user need not perform the end action, thereby simplifying measurement.

In step S105, the smartphone 1 performs calculations on the orientation information and the movement information acquired in step S103. The controller 10 performs these calculations. The controller 10 calculates the contour and girth of the cross-section of the user's abdomen. Details on the calculations in step S105 are provided below.

In step S106, the smartphone 1 outputs the results of the calculations in step S105. Examples of the method for outputting the calculated results include displaying the results on the display 2A and transmitting the results to a server. Once output of the results of calculating the contour and girth of the cross-section of the abdomen is complete, the smartphone 1 terminates the processing flow.

In this embodiment, the back face 1B of the smartphone 1 is placed against the abdomen and moved in the y-axis direction. In this case, it suffices for the direction sensor 17 to be a uniaxial sensor capable of measuring the orientation in the y-axis direction of the smartphone 1. It suffices for the acceleration sensor 16 to be a uniaxial sensor capable of measuring the movement amount in the y-axis direction.

Next, the method for calculating the contour of the cross-section is described with reference to FIGS. 7A, 7B, 8, and 9, taking the smartphone 1 as an example.

Figure 7A:
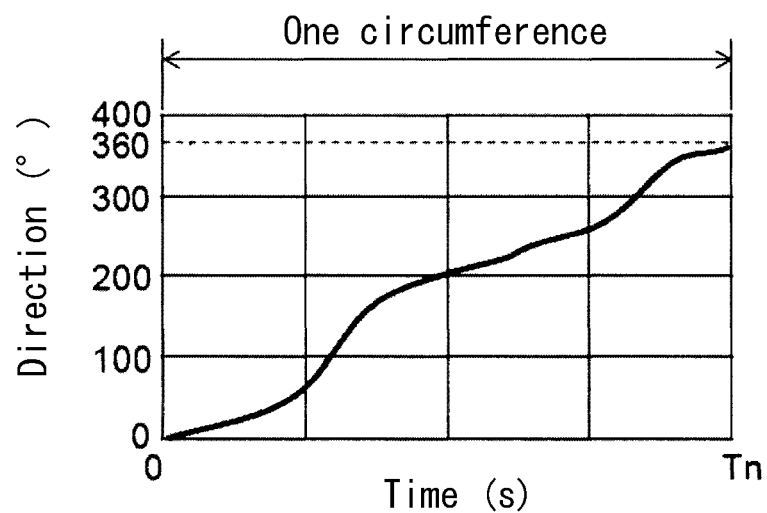
FIG. 7A illustrates an example of orientation and movement amount according to Embodiment 1.
Figure 7B:
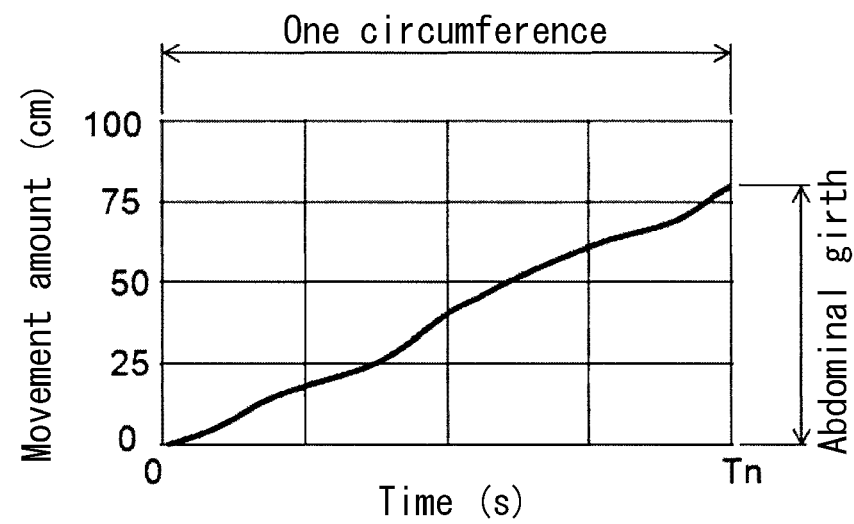
FIG. 7B illustrates an example of orientation and movement amount according to Embodiment 1.

FIGS. 7A and 7B illustrate an example of orientation and movement amount according to Embodiment 1.

The horizontal axis in FIGS. 7A and 7B indicates the time from the start to the end of measurement. Time is counted by the clock signal output by the timer 11. When the circumference of the abdomen is measured in Tn seconds (s), the start of measurement is at 0 s and the end of measurement at Tn s. Over predetermined acquisition cycles, the smartphone 1 acquires the orientation information and movement information from 0 s to Tn s. The letter n is an integer representing a record number.

In FIG. 7A, the horizontal axis represents time, and the vertical axis represents the direction of the smartphone 1. The direction of the smartphone 1 on the horizontal axis is orientation information acquired by the direction sensor 17. This embodiment adopts the direction sensor 17 as the first sensor. Hence, the orientation information is the direction of the smartphone 1. The direction of the smartphone 1 is represented as an angle from 0° to 360°. The direction of the smartphone 1 is determined to have completed one circumference upon changing 360° from the initial orientation of measurement. In this embodiment, the initial orientation of measurement is set to 0° for ease of understanding, making the orientation 360° after one circumference.

In FIG. 7B, the horizontal axis represents time, and the vertical axis represents the movement amount of the smartphone 1. The movement amount of the smartphone 1 on the vertical axis is calculated on the basis of the movement information acquired by the acceleration sensor 16. The movement information of the smartphone 1 in this embodiment is acceleration data acquired by the acceleration sensor 16. The movement amount is calculated by the controller 10 by time integrating the acceleration data twice. When the acceleration data includes a large amount of noise, digital filtering may be performed. The digital filter may, for example, be a low pass filter or a band pass filter. The movement amount of the smartphone 1 at the end of measurement corresponds to the length of the circumference of the measured part, i.e. the abdominal girth. The abdominal girth may be calculated taking into account the arrangement of the acceleration sensor 16 within the smartphone 1.

In other words, to calculate the abdominal girth accurately in this embodiment, the movement amount is corrected by taking into consideration the interval between the acceleration sensor 16 and the back face 1B, which is the opposing surface placed against the surface of the abdomen 60.

In this embodiment, the case of measuring direction and the movement amount during the same time Tn has been illustrated, but the direction and the movement amount may be measured in different times Ta and Tb. In that case, the horizontal axis of FIG. 7A may use a normalized time 0-1 normalized by Ta, the horizontal axis of FIG. 7B may use a normalized time 0-1 normalized by Tb, and the numerical values on each horizontal axis may be aligned.

FIG. 8 is an example of a record formed by acquired information.

The record number at the start of measurement is R0, and the record number at the end of measurement is Rn. In each record, orientation information and movement information corresponding to time are stored as a pair. Furthermore, the movement amount calculated on the basis of the movement information is stored in each record. In this embodiment, which uses a direction sensor, the orientation information is the direction faced by the smartphone 1. The direction and movement amount, which are information calculated on the basis of the pair of orientation information and movement information, are acquired at the same time in FIGS. 7A and 7B. The direction and movement amount may also be acquired at the same normalized time. The time intervals between the records need not be equal intervals. To accurately measure the contour of a cross-section, the record may contain a pair of information acquired at the same time, but some time lag is acceptable. When a time lag occurs, the controller 10 may ignore the time lag or may use one record to calculate information corresponding to another time.

Figure 9:
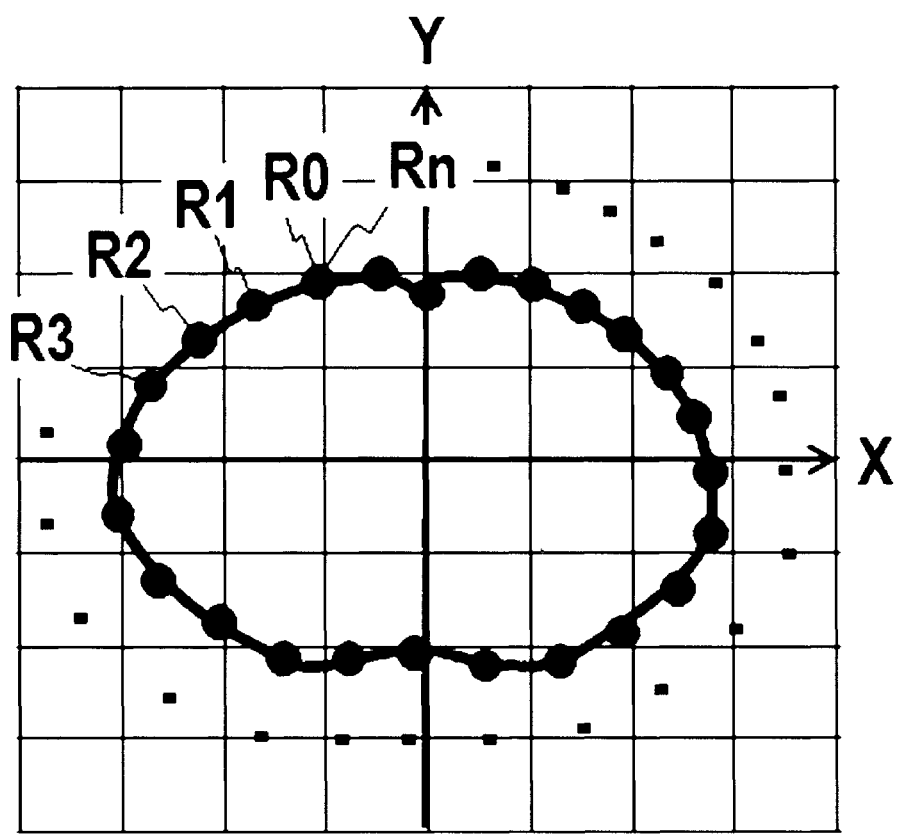
FIG. 9 illustrates the calculated contour of a cross-section according to Embodiment 1.

FIG. 9 illustrates a calculated contour of a cross-section.

The contour of a cross-section of the measured part can be calculated by plotting the acquired records R0 to Rn in order in accordance with orientation and movement amount. The labels from R0 to Rn in FIG. 9 are record numbers. The points on the solid line indicate the position of the records. The line actually includes many more points, but some of the points are omitted to clarify the drawing.

The contour of a cross-section is calculated as follows. First, R0 is set at any point. Next, the position of R1 is calculated from the amount of change in the movement amount between record R0 and record R1 and the orientation information of record R1. Next, the position of R2 is calculated from the amount of change in the movement amount between record R1 and record R2 and the orientation information of record R2. This calculation is made up to Rn. By connecting the positions in order from the position of R0 to the position of Rn, the contour of a cross-section of the measured part is calculated and then displayed.

Figure 10:
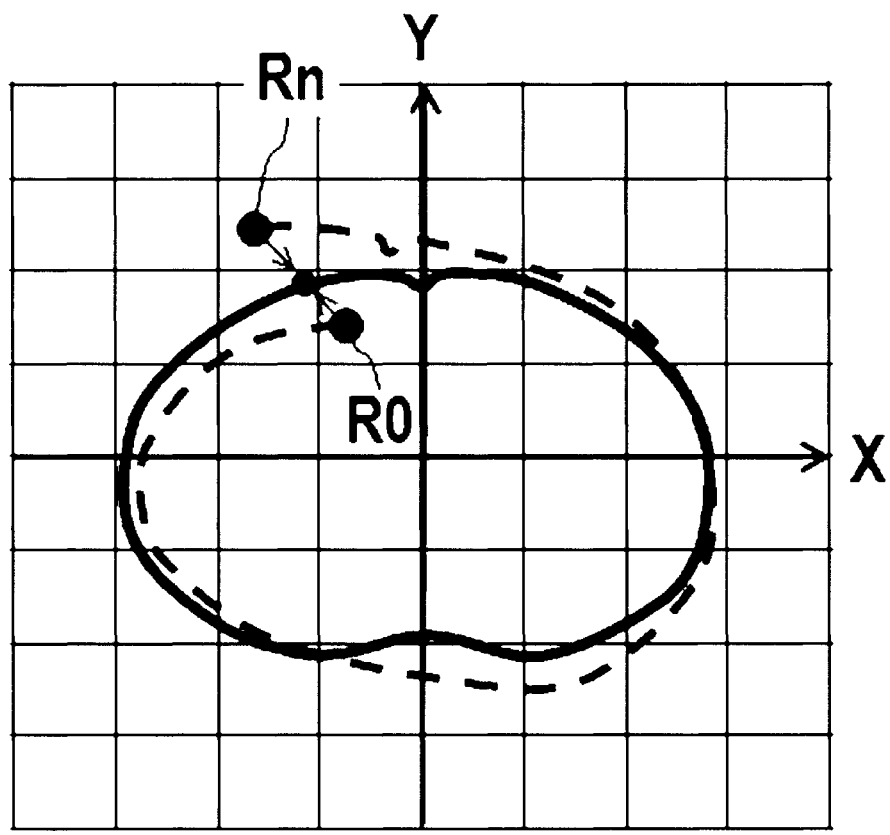
FIG. 10 illustrates correction of the calculated contour of a cross-section according to Embodiment 1.

FIG. 10 illustrates correction of the calculated contour of a cross-section.

The direction sensor and acceleration sensor both have measurement error. As a result, the movement of the smartphone 1 may shift from the A-A position, and the contour of a cross-section such as the dotted line in FIG. 10 may be calculated. In this calculation result, the measurement start point R0 and the measurement end point Rn are shifted, and an accurate contour of a cross-section has not been calculated. In such a case, as illustrated by the solid line in FIG. 10, the error is corrected by offsetting the measurement start point R0 and the measurement end point Rn so as to match.

Furthermore, each record between the measurement start point R0 and the measurement end point Rn is corrected by adding a slight offset.

Figure 11:
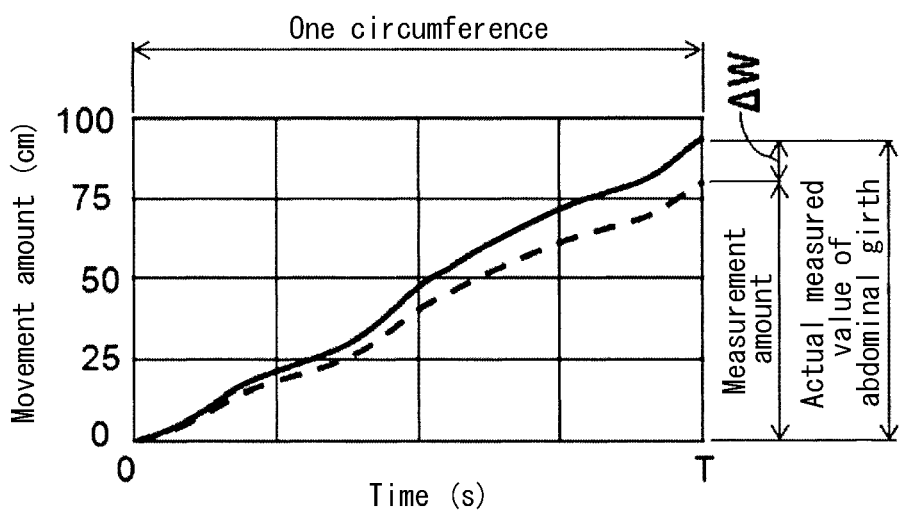
FIG. 11 illustrates correction using an actual measured value according to Embodiment 1.

FIG. 11 illustrates correction using an actual measured value according to Embodiment 1.

In the above-described embodiment, the movement information acquired by the acceleration sensor 16 is used to calculate the contour of a cross-section. If the actual measured length of the circumference of the measured part as measured in advance by other means is known, however, the contour of a cross-section can be calculated more accurately. In FIG. 11, the horizontal axis represents time, and the vertical axis represents the movement amount. The dotted line in FIG. 11 is the movement amount calculated on the basis of the movement information acquired by the acceleration sensor 16. The movement amount at the end of measurement corresponds to the length of the circumference of the measured part. In this embodiment, the movement amount corresponds to the abdominal girth. The movement amount at the end of measurement is corrected so as to equal the abdominal girth actually measured in advance by a tape measure or other instrument. In greater detail, the movement amount at the end of measurement is offset by the correction amount $\Delta W$ in FIG. 11, and the inclination of the graph is corrected to match the movement amount offset by $\Delta W$. The corrected data are indicated by a solid line. The controller 10 calculates the contour of a cross-section of the measured part using the records that are composed of the corrected, solid-line data.

Next, correction of the orientation and position of the calculated contour of a cross-section is described. Upon setting the orientation of the smartphone 1 at the start of measurement to 0°, the axis of symmetry of the calculated contour of a cross-section might be inclined. For example, in the case of the contour of an abdominal cross-section, the user may wish to correct the inclination and display the contour with the abdomen or the back directly facing the y-axis direction in FIG. 9. On the coordinate axes of FIG. 9, the inclination may be corrected by rotating the contour of the cross-section so that the width in the x-axis direction of the contour or the width in the y-axis direction of the contour is minimized or maximized.

Also, if the position coordinates of the smartphone 1 at the start of measurement are at the xy origin in FIG. 9, the calculated contour of a cross-section is displayed as being shifted from the center. In the case of the contour of an abdominal cross-section, the user may wish to correct this positional shift so that the xy origin in FIG. 9 and the center of the contour match in the display. The position may be corrected by moving, to the xy origin, the point where the widthwise center line in the x-axis direction intersects the widthwise center line in the y-axis direction of the contour of the cross-section.

As described above, in a device according to this embodiment, the contour of a cross-section of the measured part can be measured by a sensor embedded in the smartphone 1. The smartphone 1 is smaller than a measurement apparatus such as a CT apparatus. The smartphone 1 can also rapidly measure the contour of a cross-section. Users of the smartphone 1 can measure data themselves, thereby simplifying measurement. The smartphone 1 can be carried easily, which is not true of CT apparatuses and the like. Since users of the smartphone 1 can measure data themselves, they can easily recognize day-to-day changes. The smartphone 1 also entails little risk of radiation exposure during measurement.

Figure 12:
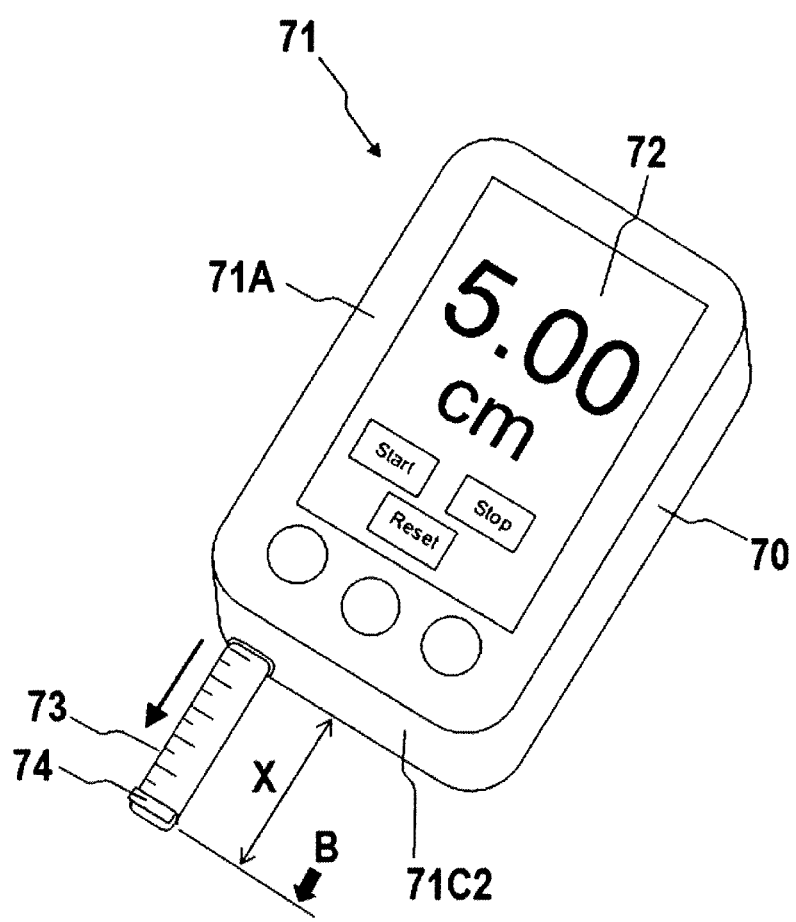
FIG. 12 schematically illustrates an electronic tape measure according to Embodiment 1.

FIG. 12 schematically illustrates an electronic tape measure according to Embodiment 1.

An electronic tape measure has a function to measure the length of extracted tape and acquire data. Hence, an electronic tape measure can acquire movement information like an acceleration sensor. The electronic tape measure may also be embedded within the smartphone 1.

An electronic tape measure 71 includes a housing 70. A touchscreen display 72 is provided on a front face 71A of the housing 70. A tape measure 73 is provided on the side face 71C2 of the housing 70. Measurement markings are inscribed on the tape measure 73. The tape measure 73 is normally wound up inside the housing 70. A stopper 74 is provided at the end of the tape measure 73. Before measurement, the stopper 74 is placed outside of the housing 70, and the B face of the stopper 74 is in contact with the side face 71C2. To measure a dimension of the measured part, the stopper 74 is pulled in the direction of the arrow in FIG. 12 to extract the tape measure 73 from the housing 70. At this time, the extracted amount X of the tape measure 73 with reference to the side face 71C2 is digitally displayed on the touchscreen display 72. The embodiment in FIG. 12 illustrates the case of X=5.00 cm.

In the case of using the electronic tape measure 71 as the second sensor of the smartphone 1 in this embodiment, the measurement procedure and the calculation of the contour of a cross-section are similar to the description in FIGS. 5 through 9. When using an electronic tape measure, the housing 70 is placed against the surface of the abdomen at the start of measurement in step S102. In step S103, the user moves the housing 70 along the surface at the A-A position of the abdomen 60 around the abdomen 60 once while holding the stopper 74 at the measurement start position. Measurement ends when the side face 71C2 and the B face of the stopper 74 match (step S104).

When using an acceleration sensor as the second sensor, the acceleration is acquired as the movement information. When using an electronic tape measure as the second sensor, the movement amount can be acquired directly as the movement information, allowing more accurate measurement of the abdominal girth.

Figure 13A:
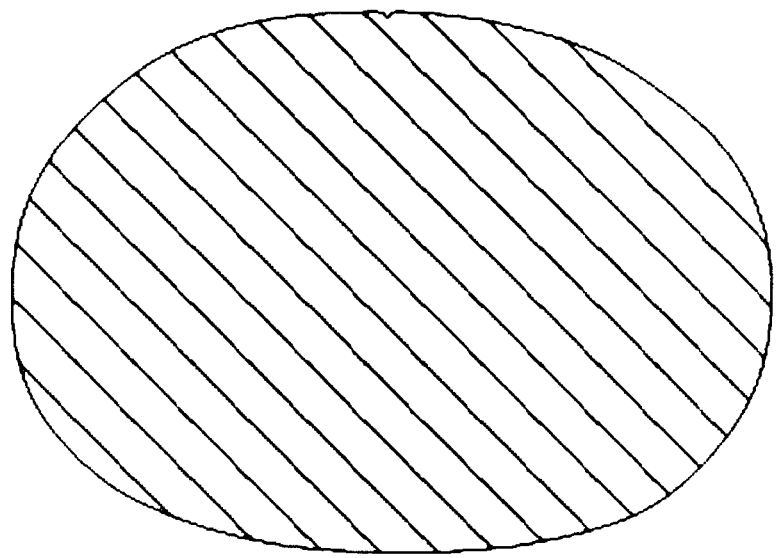
FIG. 13A is an example of the calculated contour of an abdominal cross-section according to Embodiment 1.
Figure 13B:
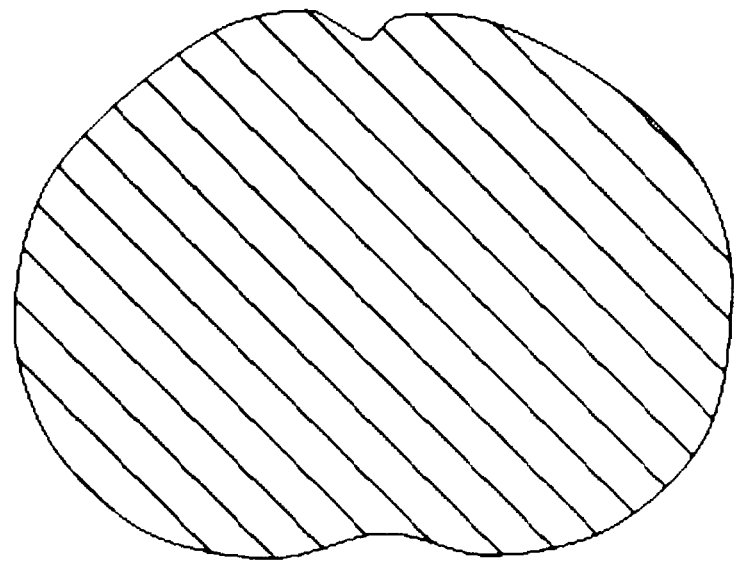
FIG. 13B is an example of the calculated contour of an abdominal cross-section according to Embodiment 1.

FIGS. 13A and 13B are examples of the calculated contour of an abdominal cross-section according to Embodiment 1.

While FIGS. 13A and 13B illustrate subjects with nearly the same abdominal girth, the subject in FIG. 13A has small muscle area, and the subject in FIG. 13B has large muscle area. Since the muscle area is small in FIG. 13A, the contour shape is close to being smooth and round. Since the muscle area is large in FIG. 13B, the shape is irregular, with several protruding locations where muscle is developed. In this way, the contour of a cross-section has a shape reflecting the characteristics of muscle area.

A method for calculating the shape characteristics of the calculated contour of an abdominal cross-section and for estimating the muscle area on the basis of the shape characteristics is described in detail in Embodiment 3.

Embodiment 2

FIG. 14 is a block diagram illustrating the configuration of a smartphone 1 according to Embodiment 2.

In this embodiment, a timer 11 and a processor 10A are included in a controller 10. The timer 11 is a device for obtaining movement information of the smartphone 1. The timer 11 receives an instruction for a timer operation from the processor 10A and outputs a clock signal. The direction sensor 17 acquires orientation information multiple times in accordance with the clock signal output from the timer 11. The orientation information acquired in accordance with the clock signal is temporarily stored inside the smartphone 1 along with clock information. Clock information refers to information indicating the time at which the orientation information was acquired. The clock information may be a record number indicating the order of acquisition when using a clock signal with a constant period, or the clock information may be the time of acquisition of the orientation information. In this embodiment, the timer 11 is included in the controller 10. A timer circuit that is a functional component of the controller 10 may be used as the timer 11. This disclosure is not limited to this example. As described above with reference to FIG. 4, the timer 11 may be provided external to the controller 10.

The processor 10A estimates the movement information of the smartphone 1 from the clock information. The movement information of the smartphone 1 is related to the movement amount of the smartphone 1. In this embodiment, the movement information is the movement amount. The processor 10A calculates a contour of a cross-section of a measured part on the basis of the movement information. The following describes the differences from Embodiment 1, omitting a description of common features.

FIG. 15 is a flowchart for measurement of the contour of an abdominal cross-section according to Embodiment 2.

In step S101, the user launches the measurement application 9Z for measuring the contour of a cross-section. After launching the measurement application 9Z, the user inputs the actual measured value of the abdominal girth, as measured in advance with a tape measure or other instrument, into the smartphone 1 (step S111). Alternatively, the actual measured value of the abdominal girth may be read from user information stored in advance in the storage 9 of the smartphone 1. The actual measured value of the abdominal girth need not be input before the start of measurement (step S102) and may instead be input after measurement is complete (step S104).

Next, measurement begins in step S102. At the start of measurement, the smartphone 1 is placed against the surface of the abdomen 60 at any position where the contour of a cross-section of the abdomen is to be measured. In this embodiment, the contour of a cross-section at the height of the user's navel (the position indicated by A-A in FIG. 5) is measured. The measurement start position may be anywhere along the abdominal A-A position. To start measurement, the user performs a preset start action on the smartphone 1. In step S103, the user moves the smartphone 1 along the surface at the A-A position of the abdomen 60. The user moves the smartphone 1 at constant speed while keeping the smartphone 1 against the surface of the abdomen 60. A support tool that facilitates movement of the smartphone may be employed so that the user can move the smartphone at constant speed. A supporting sound may also be output at constant speed from the smartphone 1 to guide the operation.

In step S103, the smartphone 1 acquires orientation information with the direction sensor 17 under pre-programmed conditions. The orientation information is acquired multiple times in accordance with the clock signal output from the timer 11. The orientation information acquired in accordance with the clock signal is stored in the smartphone 1 along with the clock information. This measurement is continuously made from the start of step S102 until the end of step S104.

The user moves the smartphone 1 around the abdomen 60 once or more at constant speed while keeping the smartphone 1 against the surface of the abdomen 60. Subsequently, the user performs a preset end action on the smartphone 1 and ends measurement (step S104). Alternatively, the smartphone 1 may end measurement automatically, without user operation, by recognizing a complete circumference when the orientation information acquired by the direction sensor 17 of the smartphone 1 matches the orientation information at the start of measurement. The smartphone 1 may also end measurement automatically, without user operation, by recognizing a complete circumference when the orientation information acquired by the direction sensor 17 of the smartphone 1 changes by 360° from the orientation information at the start of measurement. In the case of automatic recognition, the user need not perform the end action, thereby simplifying measurement.

In step S105, the processor 10A estimates the movement amount, which is the movement information of the smartphone 1, by the actual measured value of the user's abdominal girth and the clock information acquired in step S103. The circumferential movement amount of the smartphone 1 once around the user's abdominal girth is equivalent to the actual measured value of the abdominal girth input in step S111, and the smartphone 1 is considered to move at a constant speed. Therefore, the movement amount can be calculated as the movement information of the smartphone 1. The processor 10A calculates the contour of a cross-section of the measured part on the basis of the acquired orientation information and the calculated movement information.

In step S106, the smartphone 1 outputs the results of the calculations in step S105. Once output of the results of calculating the contour and girth of the cross-section of the abdomen is complete, the smartphone 1 terminates the processing flow. The other operations not described in detail in the flowchart of this embodiment conform to the operations in FIG. 6.

FIG. 16 is an example of a record constituted by acquired information according to Embodiment 2.

The record number at the start of measurement is R0, and the record number at the end of measurement is Rn. In each record, orientation information and movement information corresponding to time are stored as a pair. The movement information is the movement amount estimated from the record number or the time, each of which is clock information. The actual measured value of the user's abdominal girth is stored as the movement information of record number Rn. The time intervals between records are equal intervals, and the smartphone 1 is considered to move at a constant speed. Therefore, the interval between each movement amount, which is movement information, is also an equal interval. Records acquired in this way are displayed as a diagram indicating the contour of a cross-section.

The contour of a cross-section of the measured part can be calculated by plotting the xy coordinates of the acquired records R0 to Rn in order in accordance with orientation and movement amount. In this embodiment, each plotted point is at an equal interval in the calculated contour of a cross-section illustrated in FIG. 9. When movement of the smartphone 1 is at a constant speed at the time of measurement, the calculated contour of a cross-section has a nearly symmetrical shape about the y-axis. When movement of the smartphone 1 is not at a constant speed at the time of measurement, the calculated contour of a cross-section has a non-symmetrical, irregular shape about the y-axis. When the shape of the calculated contour of a cross-section is highly non-symmetrical, a message encouraging the user to measure again at constant speed may be displayed on the smartphone 1. The determination of the magnitude of non-symmetry may be made on the basis of the difference in the number of plotted points in each of the regions separated by the y-axis in FIG. 9. For example, when the difference in the number of plotted points is other than ±10%, the contour of the cross-section may be determined to be highly non-symmetrical. The method for determining the degree of non-symmetry is not limited to this example. For example, areas surrounded by the contour of the cross-section may be calculated and compared to determine the degree of non-symmetry. The standard for determination may also be set as necessary.

In this embodiment, by using the timer as the device for obtaining movement information of the apparatus, the movement information can be acquired without using the second sensor. Therefore, the number of components can be further reduced in the smartphone 1 of this embodiment. Furthermore, the smartphone 1 of this embodiment can reduce the measurement error caused by the accuracy of the second sensor.

A method for calculating the shape characteristics of the calculated contour of an abdominal cross-section and for estimating the muscle area on the basis of the shape characteristics is described in detail in Embodiment 3.

Embodiment 3

In Embodiment 3, muscle area is estimated from a portion of the calculated contour of a cross-section. An abdominal cross-sectional image based on the estimated muscle area is also displayed on the smartphone 1. The smartphone 1 of this embodiment may be configured in the same way as in Embodiment 1, as in the block diagram in FIG. 4, or in the same way as in Embodiment 2, as in the block diagram in FIG. 14. The following describes the differences from Embodiment 1 and Embodiment 2, omitting a description of common features.

The storage 9 stores a muscle area estimation formula created in advance. The storage 9 stores a plurality of abdominal cross-sectional images. These abdominal cross-sectional images are classified by combinations of muscle area and abdominal girth. The processor 10A calculates at least a partial contour of a cross-section of the measured part and extracts characteristic coefficients of the contour. The processor 10A reads the muscle area estimation formula stored in the storage 9 and estimates the muscle area from the extracted characteristic coefficients of the contour. Furthermore, the processor 10A extracts one image from among the plurality of abdominal cross-sectional images stored in the storage 9 and displays the image on the display 2A.

In this embodiment, an example of operations using the storage 9 and the processor 10A of the smartphone 1 is illustrated, but this disclosure is not limited to this example. A portion or all of the above-described operations may be performed using a storage and a processor installed in a server connected over a network.

In this embodiment, the angular velocity sensor 18 acquires orientation information of the smartphone 1. The timer 11 operates to obtain movement information of the smartphone 1. This disclosure is not limited to this example, and another instrument may be used to obtain the orientation information, such as a direction sensor or an inclination sensor. Also, another instrument such as an acceleration sensor or an electronic tape measure may be used to obtain the movement information.

Figure 17:
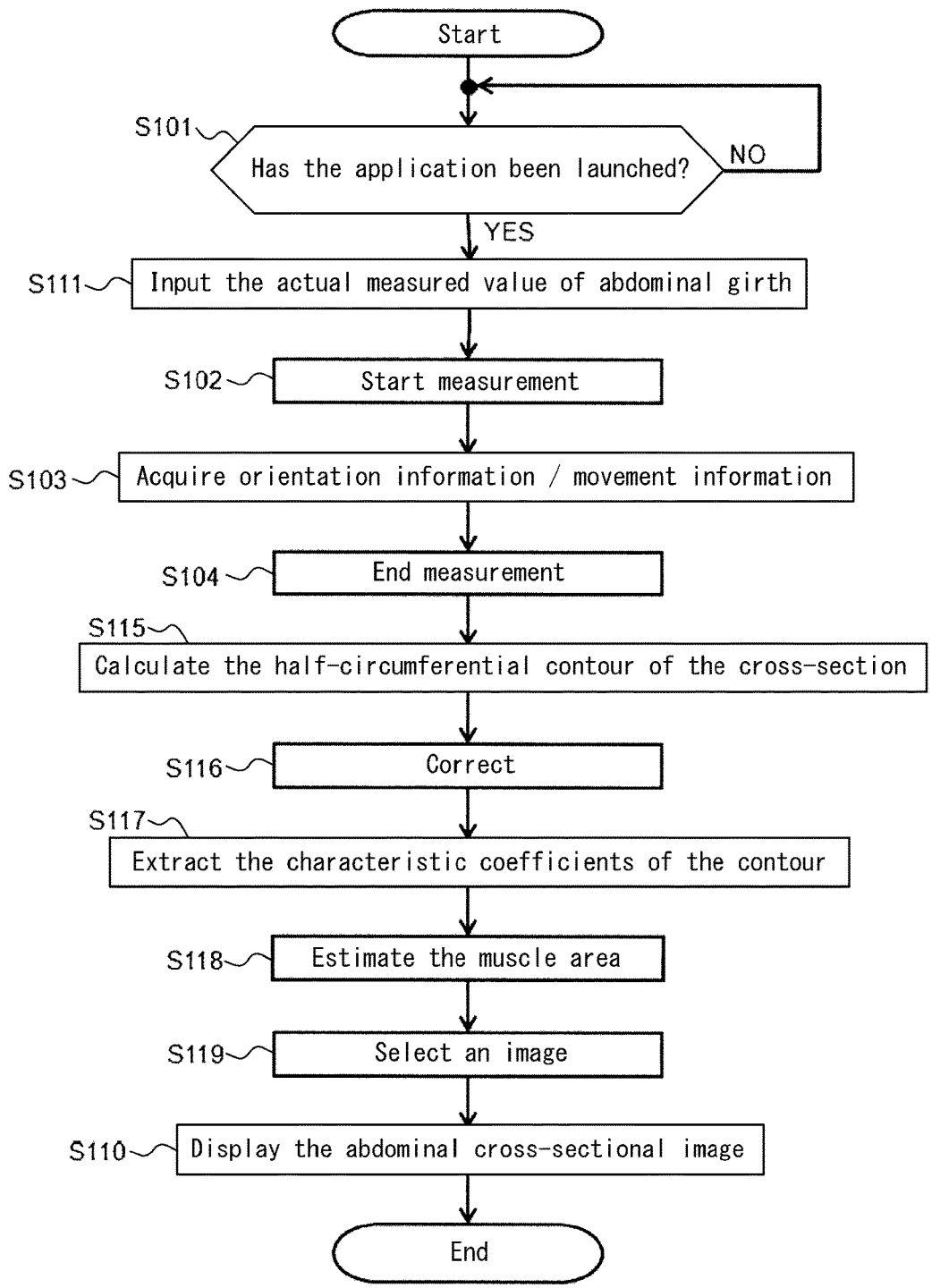
FIG. 17 is a flowchart illustrating an example of processing up to display of an abdominal cross-sectional image according to Embodiment 3.

FIG. 17 is a flowchart illustrating an example of processing up to display of an abdominal cross-sectional image according to Embodiment 3. In this embodiment, as an example of calculating at least a partial contour of an abdominal cross-section, the case of calculating the half-circumferential contour from the position of the navel is described.

In step S101, the user launches the measurement application 9Z for measuring the contour of a cross-section. After launching the measurement application 9Z, the user inputs the actual measured value of the abdominal girth, as measured in advance with a tape measure or other instrument, into the smartphone 1 (step S111). Alternatively, the actual measured value of the abdominal girth may be read from user information stored in advance in the storage 9 of the smartphone 1. Step S111 need not be performed before the start of measurement and may instead be performed after measurement in step S104 is complete. If movement information is acquired using the acceleration sensor 16 in the subsequent step S103, step S111 does not necessarily need to be performed.

Next, measurement begins in step S102. At the start of measurement, the smartphone 1 is placed against the surface of the abdomen 60 at the position of the navel. The measurement start position may be selected in accordance with the portion of the abdominal cross-section for which the contour is to be calculated. By determining the measurement start position in advance, the range of the calculated contour does not change from user to user, reducing the error in the below-described characteristic coefficients of the contour. In this embodiment, the position of the navel is the measurement start position. For example, the side face 1C1 of the smartphone 1 is matched to the position of the navel, and measurement is started. The user starts measurement by performing a preset start action on the smartphone 1.

In step S103, the user moves the smartphone 1 along the surface at the A-A position of the abdomen 60. The user moves the smartphone 1 at constant speed while keeping the smartphone 1 against the surface of the abdomen 60.

In step S103, the smartphone 1 acquires the angular velocity (°/s), which is orientation information, with the angular velocity sensor 18 under pre-programmed conditions. The orientation information is acquired multiple times in accordance with the clock signal output from the timer 11. The orientation information acquired in accordance with the clock signal is stored in the smartphone 1 along with acquired time information. This measurement is continuously made from the start of step S102 until the end of step S104. The movement amount may be measured as the movement information by the acceleration sensor 16. Since the movement information acquired by the acceleration sensor 16 is similar to the movement information described in Embodiment 1, further description is omitted.

The user moves the smartphone 1 around the abdomen 60 over half or more of the circumference at constant speed while keeping the smartphone 1 against the surface of the abdomen 60. In this embodiment, half of the circumference refers to moving from the navel to the center of the back. Calculation of the contour is insufficient if the smartphone 1 is not moved over half of the circumference, and error may occur in the below-described characteristic coefficients of the contour. Accordingly, the smartphone 1 may include means for notifying the user of half of the circumference.

After moving the smartphone 1 over half or more of the circumference, the user performs a preset end action on the smartphone 1 and ends measurement (step S104). Alternatively, if the below-described step S115 is executed simultaneously, the smartphone 1 may end measurement automatically by recognizing nearly half of the circumference when the orientation of the smartphone 1 changes 180° from the start of measurement. With such automatic recognition, the user need not perform the end action, thereby simplifying measurement.

After the end of measurement or during measurement, the processor 10A calculates the half-circumferential contour of the abdominal cross-section (step S115). The processor 10A calculates the orientation of the smartphone 1 by integrating the angular velocity, acquired in step S103, once.

Figures 18, 19:
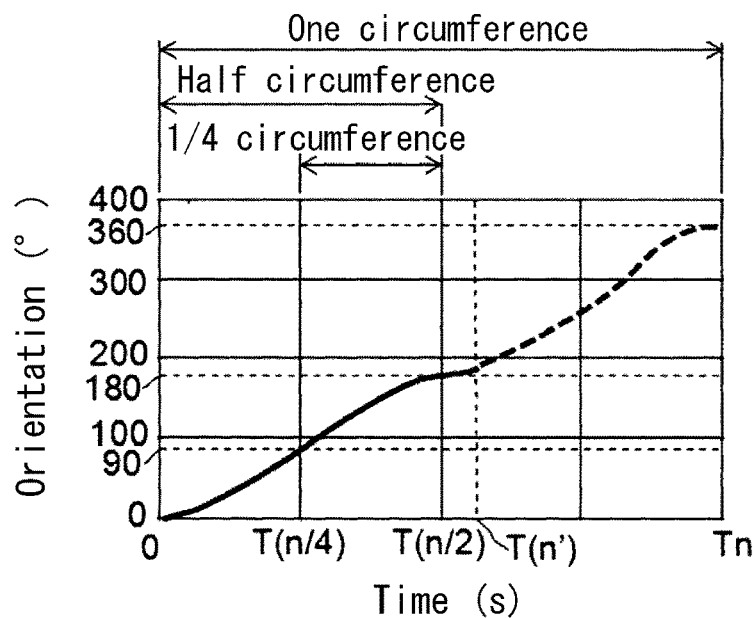
FIG. 18 is an example of the orientation of a smartphone 1 according to Embodiment 3.
FIG. 19 is an example of a record constituted by acquired information according to Embodiment 3.

FIG. 18 illustrates an example of the orientation of the smartphone 1 according to Embodiment 3. With reference to FIG. 18, the method for extracting information on half of the circumference from the acquired orientation information is described. The horizontal axis represents time. The measurement start time is 0 s, and the measurement end time is T(n') s. The letter n' is an integer representing the last acquired record number. Here, n/2 is an integer representing the record number at half of the circumference. The vertical axis represents the orientation of the smartphone 1. The solid line represents acquired information, whereas the dotted line is an imaginary line of non-acquired information for the full circumference. The flat portion where the orientation is near 180° along the line in FIG. 18 is estimated as information on the back. The center of the back is determined to have been passed at the center of this flat portion, and half of the circumference is detected. In other words, the time T(n/2) s after 0 s in FIG. 18 is extracted as information on half of the circumference. This method of extracting information on half of the circumference is only an example. For example, when the flat portion is at a position shifted from 180°, the flat portion may be normalized to 180°. Normalization may also be performed by setting information on the position where the orientation is −180° from the flat portion as the starting point. Rather than the center of the flat portion, information on the position where the inclination of the curve is smallest near where the orientation is 180° may be determined to be the center of the back.

FIG. 19 is an example of a record constituted by acquired and normalized information according to Embodiment 3. The extracted starting point of the half-circumferential contour (in this embodiment, the position of the navel) is set to record number R0, half of the circumference (in this embodiment, the record where the orientation is 180° at the center of the back) is set to record R(n/2), and the last acquired information is set to record R(n'). In each record, orientation information and movement information are stored as a pair. The movement information is the movement amount estimated from the record number (or the time), which is clock information. In this embodiment, records for an orientation of 0° to 180° are extracted as information on half of the circumference. Half of the actual measured value of the user's abdominal girth is stored as the movement information of record number R(n/2). The time intervals between records are equal intervals, and the smartphone 1 is considered to move at a constant speed. Therefore, the interval between each movement amount, which is movement information, is also an equal interval. Records acquired in this way are displayed as a diagram indicating the half-circumferential contour of a cross-section. The half-circumferential contour of a cross-section of the measured part can be calculated by plotting the xy coordinates of the acquired records R0 to R(n/2) in order in accordance with orientation and movement amount. Step S115 may be executed in parallel with step S103.

In step S116, the smartphone 1 corrects the results of the calculations in step S115. This correction is preprocessing for extracting the characteristic coefficients of the contour in the following step S117. The characteristic coefficients of the contour change depending on factors such as the orientation and position of the contour on an arbitrary xy coordinate system. In this embodiment, the orientation of the contour refers to the below-described orientation of the axis of symmetry, and the position of the contour refers to the below-described position of the center point. By correcting factors such as the orientation of the contour and the position of the contour, variation in the characteristic coefficients of the contour as caused by measurement conditions can be reduced. The orientation of the contour and the position of the contour are easily corrected on the basis of an inverted closed curve yielded by folding the calculated half-circumferential contour of the cross-section over an axis of symmetry defined by a line connecting the starting point and the ending point (in this embodiment, the position of the navel and the center of the back, respectively). To correct the orientation of the contour, the inverted closed curve is rotated so that the axis of symmetry of the inverted closed curve (the line connecting the navel and the center of the back) faces a predetermined direction. To correct the position of the contour, the inverted closed curve is moved so that the center point of the inverted closed curve matches the origin of the coordinate system. The orientation and position may be corrected by a known method.

Figure 20:
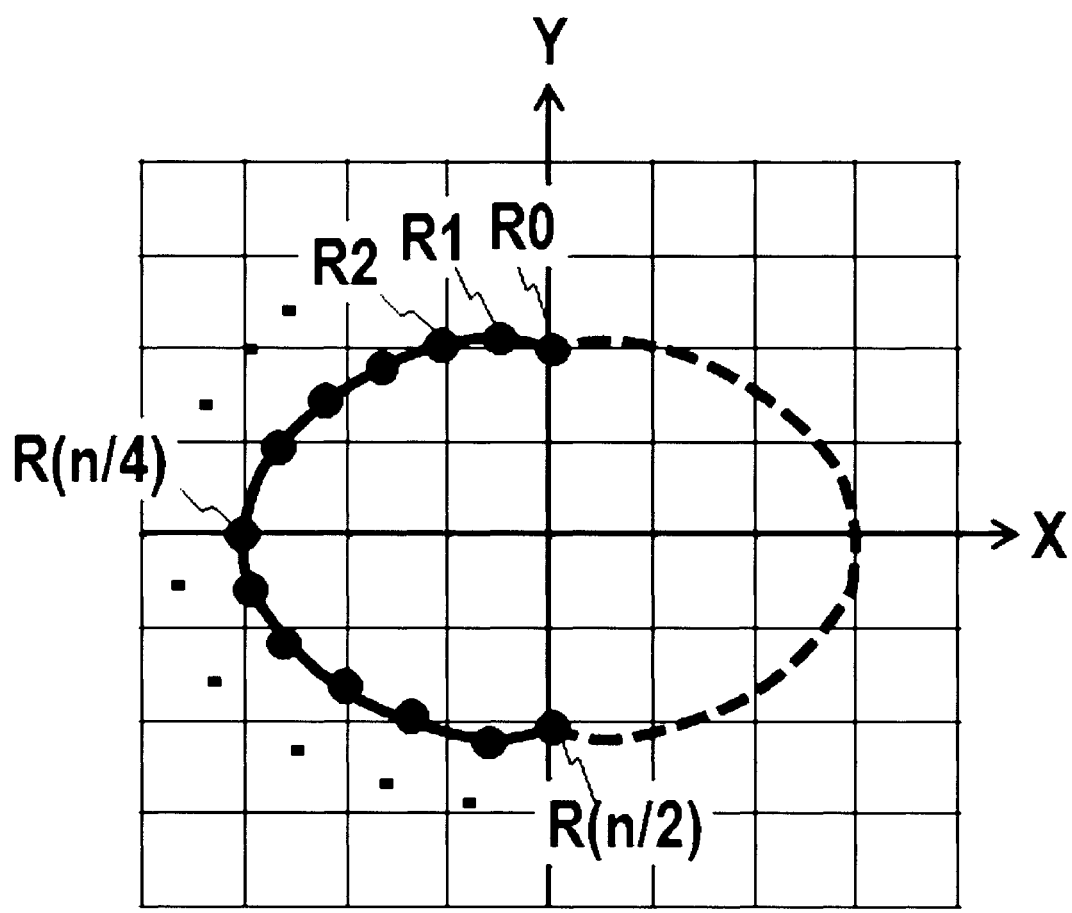
FIG. 20 illustrates a calculated and corrected contour of a cross-section according to Embodiment 3.

FIG. 20 illustrates a calculated and corrected contour of a cross-section according to Embodiment 3. The solid line in the graph is the calculated half-circumferential contour of the cross-section, and the dotted line is the imaginary line when the calculated half-circumferential contour of the cross-section is rotated about the axis of symmetry. The black dots are plots of the acquired records on the xy coordinates.

After the correction in step S116, the smartphone 1 extracts the characteristic coefficients of the contour of the cross-section (step S117). In this embodiment, the method for extracting the characteristics of the contour uses Fourier analysis. By performing Fourier analysis on the curve of the half-circumferential contour of the cross-section or on the inverted closed curve, the Fourier coefficients can be sought. As is well known, the Fourier coefficients of different orders that are sought when the curve is subjected to Fourier analysis are used to indicate the characteristics of the curve. The orders of Fourier coefficients that are extracted as characteristic coefficients are determined when creating estimation formulas, which are described below in detail. In this embodiment, the Fourier coefficients Sa1, Sa2, Sa3, and Sa4 that affect muscle area are extracted as characteristic coefficients of the contour. If the independent variables of the estimation formula are taken to be the principal components when creating each estimation formula, then the principal components may be extracted as the characteristic coefficients.

The smartphone 1 estimates the user's muscle area A by substituting the characteristic coefficients Sa1 to Sa4 extracted in step S117 into the muscle area estimation formula sought in advance (step S118). An example of the muscle area estimation formula is illustrated in Equation 1.

$$A = 20.9 + 108.2 \times Sa_1 - 345.2 \times Sa_2 - 72.6 \times Sa_3 - 224.5 \times Sa_4$$

Details on the method for creating the muscle area estimation formula are provided below.

Next, on the basis of the muscle area A estimated in step S118, the smartphone 1 selects the closest image to the user's abdominal cross-section (step S119).

FIG. 21 illustrates an example of a classification table of abdominal cross-sectional images according to Embodiment 3. This classification table is for men. The smartphone 1 stores the classification table illustrated in FIG. 21 in advance. In this embodiment, 25 types of images (P11 to P55) with different muscle area and abdominal girth are stored in the smartphone 1. The 25 types of images may be CT images, patterns based on these images, or marks. From among the 25 types of images, one image corresponding to the user's estimated muscle area A and abdominal girth is selected.

The selected image is displayed on the display 2A of the smartphone 1 (step S110).

According to Embodiment 3, all of the steps are executed by the smartphone 1, but this disclosure is not limited to this configuration. At least a portion of the steps may be executed by a server or other apparatus connected over a network. For example, the measurement steps S102 to S104 and the display step S110 may be executed by the smartphone 1, with the other steps being executed by a server connected over a network. By performing complicated calculations on the server, the processing speed from start to finish can be improved.

According to Embodiment 3, an image is displayed, allowing the user's state of muscle accumulation to be conveyed simply without performing an abdominal CT scan. When displaying an abdominal CT image, the user's estimated abdominal cross-sectional shape can be visualized more realistically. For example, such visualization is useful for training. By numerical values of the muscle area being displayed together with an image, the user can be concretely notified of the state of muscle accumulation. Also, users themselves can perform measurements daily, which facilitates awareness of the effects of training.

Figure 22:
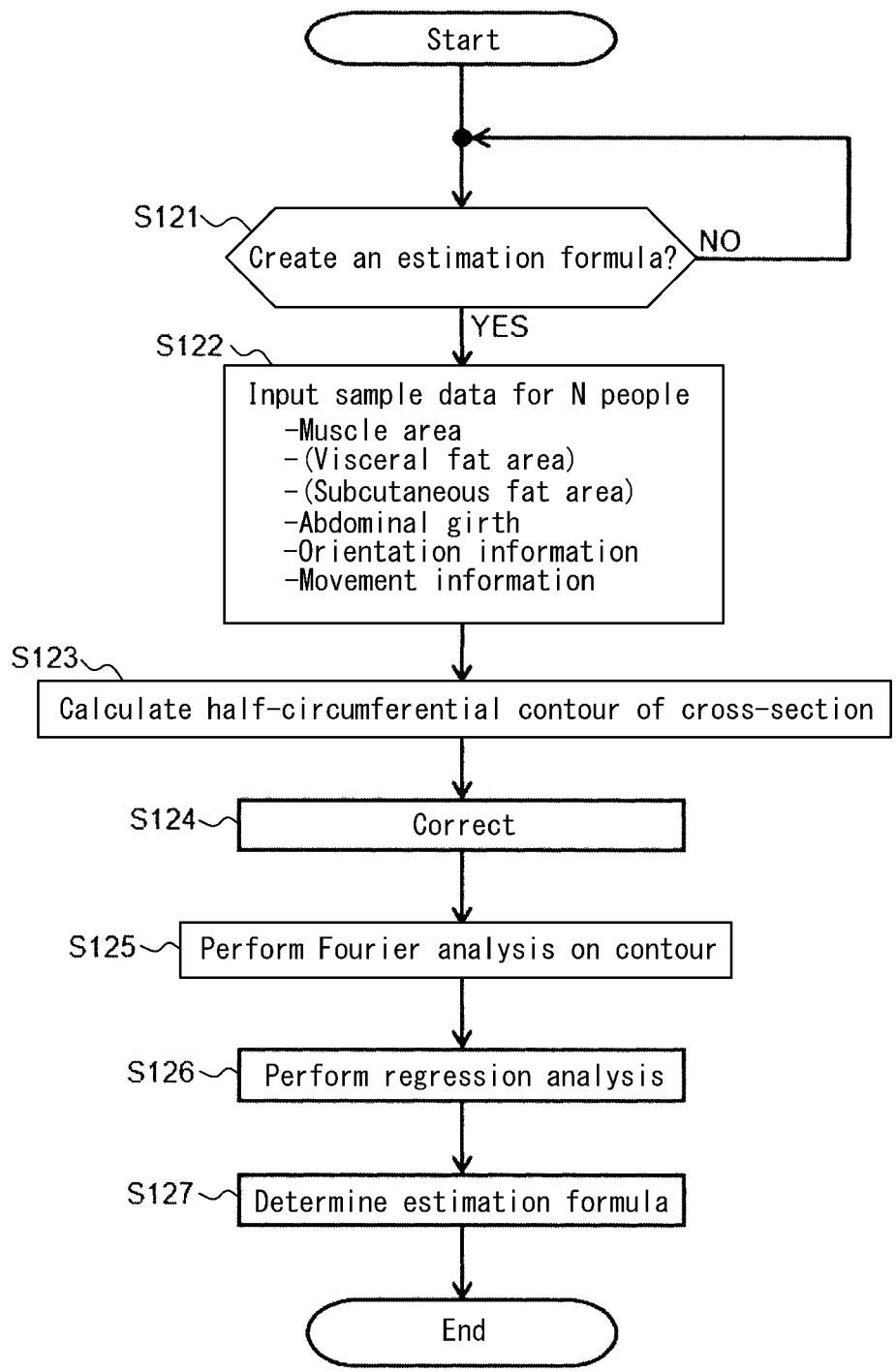
FIG. 22 is a flowchart for creating a muscle area estimation formula according to Embodiment 3.

FIG. 22 is a flowchart for creating a muscle area estimation formula according to Embodiment 3. The procedure for creating muscle area estimation formulas is described with reference to FIG. 22. These estimation formulas need not be created on the smartphone 1 and may be calculated in advance on another apparatus, such as a computer. The created estimation formulas are read into the application in advance. Therefore, the user need not create or change the estimation formulas directly.

In step S121, the creator creates an estimation formula. In step S122, the creator of the estimation formula inputs sample data, acquired in advance, for a predetermined number of people into the computer. The sample data are acquired from a predetermined number of sample subjects. The sample data for one subject at least include the muscle area obtained by a CT, the abdominal girth measured by a tape measure or other instrument, orientation information acquired by the smartphone 1, and movement information. The predetermined number of people may be any statistically sufficient number. The estimation accuracy improves by adopting constant conditions, such as sex, race, and age group, for the subjects.

Next, the computer calculates the half-circumferential contour of the cross-section from the input abdominal girth, orientation information, and movement information (step S123). The computer also corrects the calculated half-circumferential contour of the cross-section (step S124). Since steps S123 and S124 are the same processing as the above-described steps S115 and S116, a detailed description is omitted.

Next, Fourier analysis is performed on the calculated and corrected curve of the half-circumferential contour of the cross-section or on the inverted closed curve (step S125). By subjecting the contour of the cross-section to Fourier analysis, a plurality of Fourier coefficients can be sought. As is well known, the Fourier coefficients of different orders that are obtained when the curve is subjected to Fourier analysis are used to represent the characteristics of the curve. In this embodiment, the sample data for a predetermined number of people are subjected to Fourier analysis to seek the x-axis, y-axis, and $1^{st}$ to $k^{th}$ order Fourier coefficients (where k is any integer). Furthermore, the Fourier coefficients may be subjected to well-known principal component analysis to reduce the number of dimensions. As the analysis method for principal component analysis, a common component may be sought for multivariate data (in this embodiment, a plurality of Fourier coefficients), and a type of composite variable (principle component) may be created. The characteristics of the curve can thus be represented with even fewer variables.

Next, regression analysis is performed on the muscle area obtained by the plurality of Fourier coefficients (or principle components) sought in step S125 and by CT (step S126). Regression analysis refers to a statistical method for examining and clarifying the relationship between a numerical value representing a result and a numerical value representing a cause. With the Fourier coefficients (or principle components) as independent variables and the muscle area obtained by CT as a dependent variable, regression analysis is performed using the data of a predetermined number of sample subjects to create a muscle area estimation formula.

Equation 1 above is an example of the created estimation formula. The independent variables Sa1, Sa2, Sa3, and Sa4 in Equation 1 are the characteristic coefficients that estimate the user's muscle area. In this way, the estimation formula for muscle area can be created by the above-described statistical means (such as principal component analysis and regression analysis).

In step S122, the creator may input the visceral fat area and the subcutaneous fat area that are obtained by CT along with the muscle area. At this time, the input visceral fat area and subcutaneous fat area are used as independent variables along with the coefficients, sought in step S125, that represent the characteristics of the shape. The creator may create the muscle area estimation formula by performing regression analysis with these independent variables and with the muscle area, obtained by CT, as the dependent variable. By adding the visceral fat area and the subcutaneous fat area obtained by CT as independent variables, the estimation accuracy of the muscle area can be improved.

As described above, according to the smartphone 1 of this embodiment, the half-circumferential contour of an abdominal cross-section can be measured easily and accurately. Hence, the muscle area can quickly be estimated accurately.

Also, the contour of a person's abdominal cross-section is nearly symmetrical. Therefore, by simply calculating at least the half-circumferential contour of a cross-section, the smartphone 1 of this embodiment can estimate the muscle area of the abdominal cross-section. As a result, it suffices for the user to move the smartphone 1 around at least half of the abdomen, thereby shortening the measurement time. Furthermore, the smartphone 1 no longer needs to be switched between hands during measurement, making it easier to move the smartphone 1 at a constant speed and improving measurement accuracy.

In this disclosure, the contour of a particular portion that is less than half of the circumference may be calculated. For example, by calculating the contour of the back portion of the erector spinae muscles, which are important muscles supporting the body, and extracting characteristic coefficients, the muscle area of the erector spinae muscles can be estimated.

Figure 23:
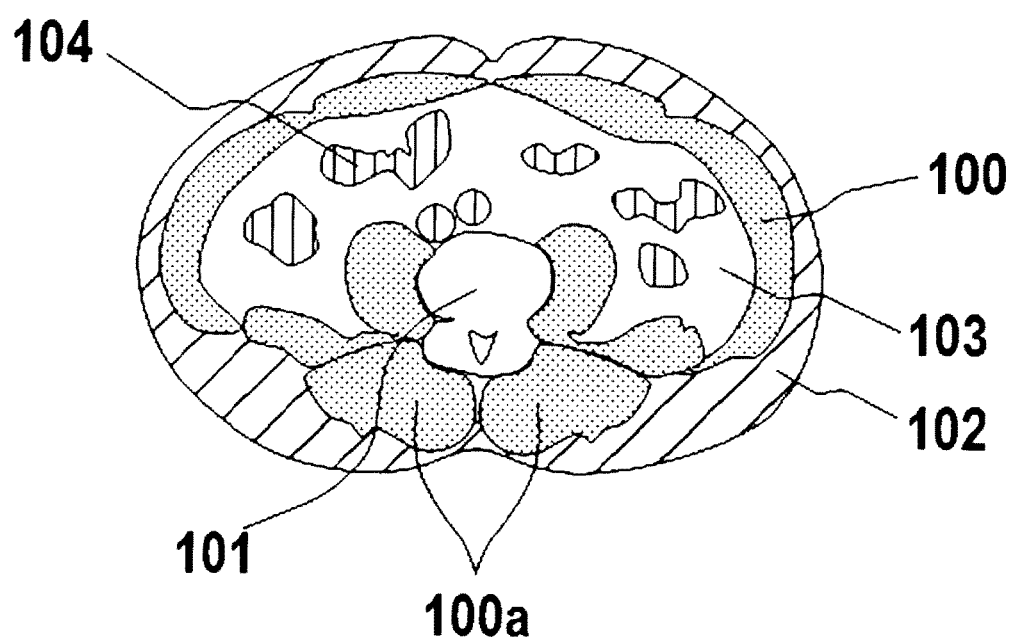
FIG. 23 illustrates an abdominal cross-section.

FIG. 23 illustrates an abdominal cross-section of an adult. FIG. 23 illustrates muscles 100; the erector spinae muscles 100a, which are muscles located on the dorsal side of the spinal column; the backbone 101; subcutaneous fat 102; visceral fat 103; and organs 104.

As can be seen in FIG. 23, the erector spinae muscles 100a are nearly symmetrical with respect to the center of the back. In this disclosure, the muscle area of the 23 erector spinae muscles 100a can be estimated from the characteristics of the abdominal contour. First, the partial contour where the erector spinae muscles 100a are located, such as a ¼ circumferential contour from where the orientation of the smartphone 1 changes from 90° to 180°, is calculated. The characteristic coefficients of the contour are then extracted and the muscle area of the erector spinae muscles 100a is estimated.

For example, the case of calculating the ¼ circumference behind the erector spinae muscles 100a is described. The processing flow may be modified so that in step S115 of the flowchart in FIG. 17, the ¼ circumference of the contour of the cross-section is calculated. For example, a determination of nearly ¼ of the circumference is made when the orientation of the smartphone 1 changes from 90° to 180°, and the ¼ circumferential contour is calculated. In greater detail, in the graph of the orientation of the smartphone 1 in FIG. 18, the portion of the graph where the orientation is from 90° to 180° is extracted as information on the ¼ circumference. In other words, in FIG. 19, the records for the orientation from 90° to 180° are extracted as information on the ¼ circumference.

Figure 24:
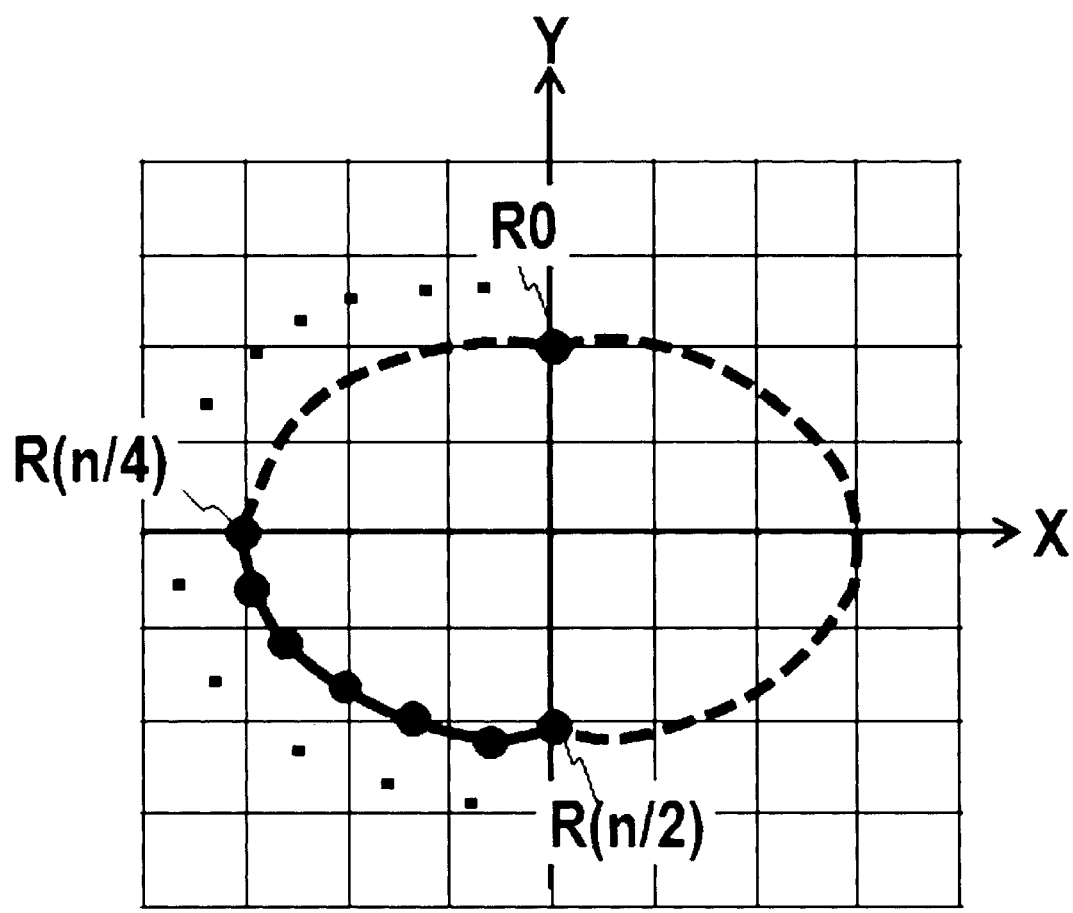
FIG. 24 illustrates a calculated and corrected contour of a cross-section according to Embodiment 3.

FIG. 24 illustrates a contour of a cross-section calculated on the basis of orientation information and movement information extracted for the ¼ circumference. In FIG. 24, the bold solid line is the calculated ¼ circumferential contour of a cross-section, whereas the dotted line is the result of correcting the calculated ¼ circumferential contour of a cross-section to become a closed curve. For example, the contour may be corrected on the basis of the inverted closed curve that is folded with the x-axis and y-axis in the coordinate system as the axes of symmetry or on the basis of a closed curve yielded by connecting a predetermined curve to an inverted curve that is folded with the y-axis as the axis of symmetry.

By simply calculating at least a partial contour of a cross-section, the smartphone 1 of this embodiment can estimate the muscle area of the abdominal cross-section. Therefore, the measurement time can be shortened. Furthermore, the smartphone 1 need not be rotated beyond the back, making it easier to move the smartphone 1 at a constant speed and improving measurement accuracy.

Although examples of calculating the half-circumferential and ¼ circumferential contour have been described, this disclosure is not limited to these examples. The cross-sectional contour may be calculated and the muscle area estimated for any portion.

Next, an experiment was performed to confirm the effects of this embodiment. Measurement was made using a Kyocera smartphone (model number WX10K). The muscle area was estimated by calculating the half-circumferential contour of a cross-section and using the characteristic coefficients of the contour corrected by an inverted closed curve. The estimation formula of the muscle area was determined using, as independent variables, the coefficients representing the shape characteristics of the contour. For a first group (25 males aged 20 to 69), the correlation between the estimated muscle area and the muscle area obtained by CT was evaluated as a correlation coefficient. A high correlation coefficient of 0.96 was obtained as a result, confirming the effects of this disclosure. Similar evaluation was also made for a second group (41 males aged 20 to 69). The resulting correlation coefficient was 0.70. A correlation was thus confirmed, although the effect was less than for the first group. The variation in the subcutaneous fat area was greater in the second group than in the first group. This variation was thought to be the reason for the lower correlation coefficient. The muscle area was therefore estimated with an estimation formula determined using, as independent variables, the subcutaneous fat area along with the coefficients representing the shape characteristics of the contour. A higher correlation coefficient of 0.88 was obtained as a result, confirming the effects of this disclosure.

Figure 25A:
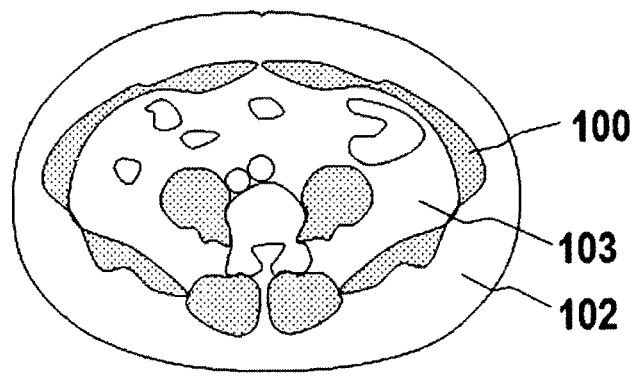
FIG. 25A is an example of an abdominal cross-sectional image displayed on the smartphone 1 of this disclosure.
Figure 25B:
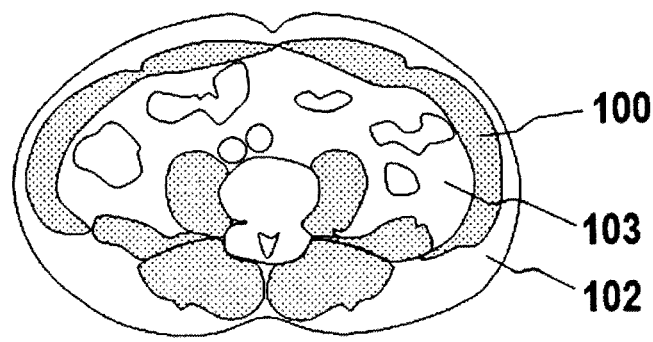
FIG. 25B is an example of an abdominal cross-sectional image displayed on the smartphone 1 of this disclosure.
Figure 25C:
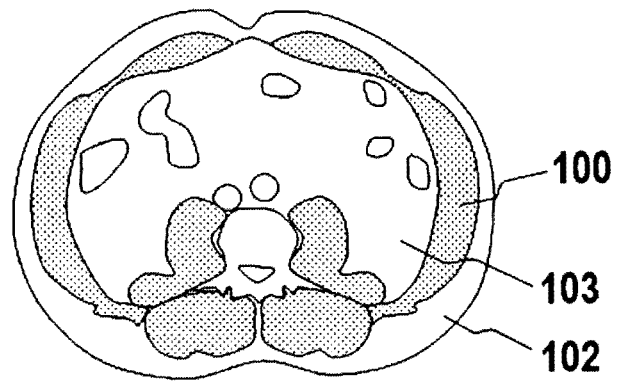
FIG. 25C is an example of an abdominal cross-sectional image displayed on the smartphone 1 of this disclosure.

FIGS. 25A, 25B, and 25C are examples of an abdominal cross-sectional image displayed on the smartphone 1. FIG. 25A is an image classified as an abdominal girth of 101 cm or greater and muscle area of 101 $cm^2$ to 150 $cm^2$ (P35 in FIG. 21). FIG. 25B is an image classified as an abdominal girth of 81 cm to 90 cm and a muscle area of 201 $cm^2$ or greater (P53 in FIG. 21). On the basis of the estimated muscle area and the abdominal girth, the smartphone 1 displays these CT images or schematic diagrams of these CT images. With this display of CT images or schematic diagrams of CT images, the user's abdominal cross-sectional shape can be visualized more realistically. Such visualization is useful for muscle training.

In this embodiment, an example of one image being selected on the basis of estimated muscle area and abdominal girth has been illustrated, but this disclosure is not limited to this example. For example, using a method similar to estimation of muscle area, the visceral fat area and subcutaneous fat area may be estimated from the characteristic coefficients of the abdominal contour. One image may then be selected on the basis of the estimated muscle area, the visceral fat area, and the subcutaneous fat area. As compared to the image in FIG. 25B, the image in FIG. 25C has nearly the same abdominal girth, muscle area, and subcutaneous fat area, but has a larger visceral fat area. With a display of CT images or schematic diagrams of CT images on the basis of the estimated muscle area, visceral fat area, and subcutaneous fat area, the user's abdominal cross-sectional shape can be visualized more realistically. Such visualization is useful for increasing the user's health awareness.

Embodiment 4

In Embodiment 4, the muscle area in a thigh cross-section is estimated. The smartphone 1 of this embodiment may be configured in the same way as in Embodiment 1, as in the block diagram in FIG. 4, or in the same way as in Embodiment 2, as in the block diagram in FIG. 14. The following describes the differences from Embodiments 1 to 3, omitting a description of common features.

The storage 9 in FIG. 14 stores a thigh muscle area estimation formula created in advance. The storage 9 stores a plurality of thigh cross-sectional images. These thigh cross-sectional images are classified by muscle area. The processor 10A calculates the contour of the thigh and extracts characteristic coefficients of the contour. The processor 10A reads the thigh muscle area estimation formula stored in the storage 9 and estimates the thigh muscle area from the extracted characteristic coefficients of the contour. Furthermore, the processor 10A extracts one image from among the plurality of thigh cross-sectional images stored in the storage 9 and displays the image on the display 2A.

Figure 26:
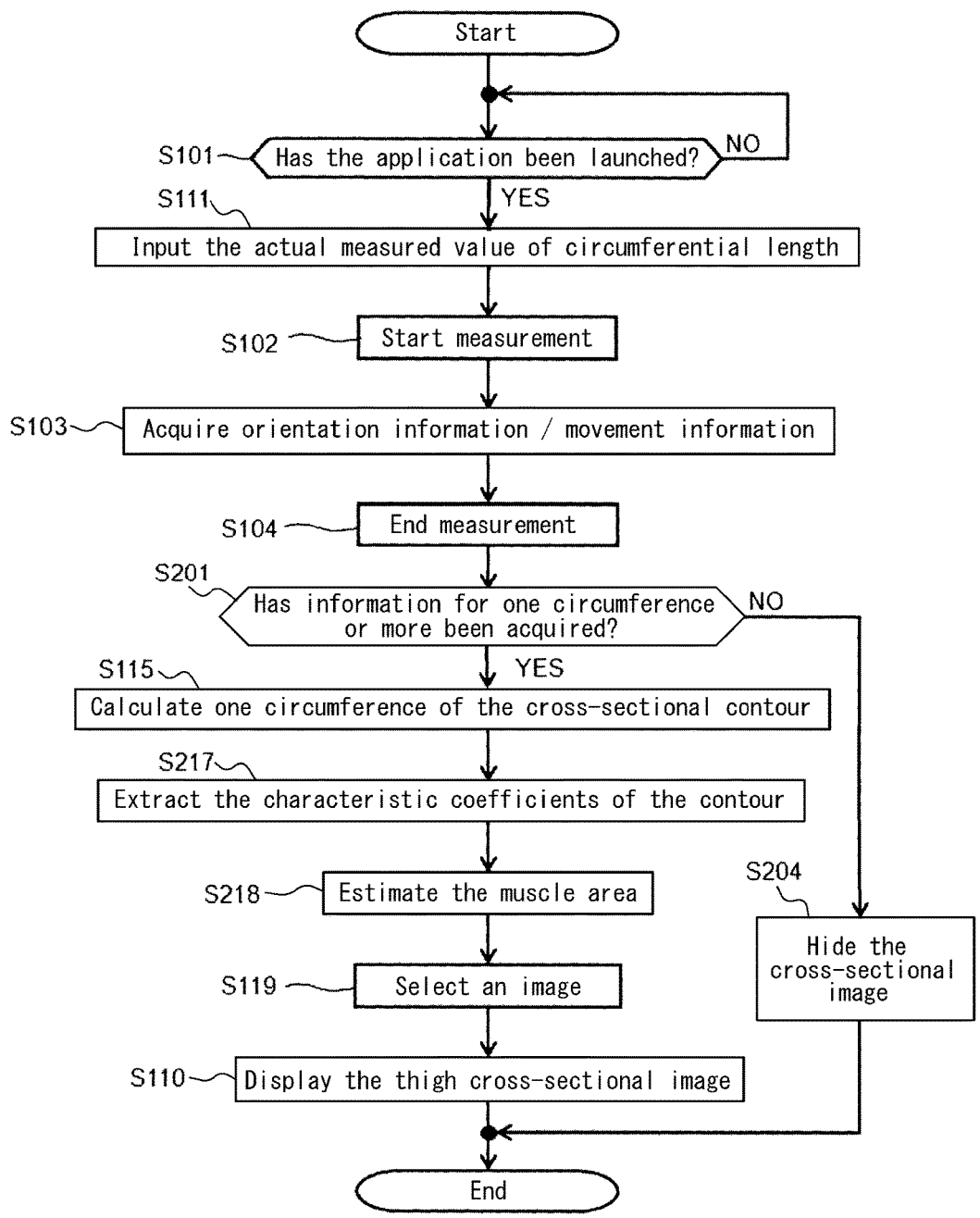
FIG. 26 is a flowchart illustrating an example of processing up to display of a thigh cross-sectional image according to Embodiment 4.

FIG. 26 is a flowchart illustrating an example of processing up to display of a thigh cross-sectional image according to Embodiment 4. As an example in this embodiment, the thigh contour at a position approximately 15 cm below the crotch is calculated. I have observed that measuring while the thigh is flexed allows for muscle area to be estimated more accurately than when measuring while the thigh is not flexed. Therefore, in this embodiment, contour information is acquired on the thigh when the thigh is flexed.

In step S101, the user launches the measurement application 9Z for measuring the contour of a cross-section. After launching the measurement application 9Z, the user inputs the actual measured value of the circumferential length of the thigh, as measured in advance with a tape measure or other instrument, into the smartphone 1 (step S111). Alternatively, the actual measured value of the circumferential length of the thigh may be read from user information stored in advance in the storage 9 of the smartphone 1. Step S111 need not be performed before the start of measurement and may instead be performed after measurement in step S104 is complete. If movement information is acquired using the acceleration sensor 16 in step S103, step S111 does not necessarily need to be performed.

Next, measurement begins in step S102. In this embodiment, the front surface of the thigh is the measurement start position. The user starts measurement by performing a preset start action on the smartphone 1.

In step S103, the user moves the smartphone 1 along the surface of the thigh. The user moves the smartphone 1 at constant speed while keeping the smartphone 1 against the surface of the thigh.

In step S103, the smartphone 1 acquires the angular velocity (°/s), which is orientation information, with the angular velocity sensor 18 under pre-programmed conditions. The orientation information is acquired multiple times in accordance with the clock signal output from the timer 11. The orientation information acquired in accordance with the clock signal is stored in the smartphone 1 along with acquired time information. This measurement is continuously made from the start of step S102 until the end of step S104. The movement amount may be measured as the movement information by the acceleration sensor 16. Since the movement information acquired by the acceleration sensor 16 is similar to the movement information described in Embodiment 1, further description is omitted.

In the process of executing step S103, the processor 10A may emit a sound from the receiver 7 or other component of the smartphone 1 at constant time intervals. By moving the smartphone 1 while hearing the sound at constant time intervals, the user can easily move the smartphone 1 at a constant speed around the thigh.

The user moves the smartphone 1 around the thigh once or more at constant speed while keeping the smartphone 1 against the surface of the thigh. The smartphone may notify the user that data for one circumference has been acquired.

After moving the smartphone 1 over the circumference once or more, the user performs a preset end action on the smartphone 1 and ends measurement (step S104). Alternatively, the processor 10A may end measurement automatically by recognizing nearly one circumference when the orientation of the smartphone 1 changes 360° from the start of measurement. With such automatic recognition, the user need not perform the end action, thereby simplifying measurement.

The user may also end measurement with an end action upon recognizing a notification from the smartphone 1 that data for 360° (one circumference) has been acquired.

Even when the movement of the smartphone 1 is less than one circumference, the processor 10A may automatically end measurement when detecting an abnormality, such as that the orientation information does not change for a certain length of time, or when the orientation switches from increasing to decreasing or vice versa.

Upon the end of measurement (step S104), the processor 10A determines whether information for one circumference or more has been acquired (step S201). This determination may be made by, for example, determining whether the orientation information at the end of measurement is 360° or greater in FIG. 7A and FIG. 7B. The processor 10A may also determine whether data for one circumference or more has been acquired on the basis of the time at which measurement ended in step S104.

Upon determining in step S201 that information for one circumference or more has been acquired, the processor 10A calculates the contour of one circumference of the thigh cross-section as in Embodiment 2 (step S115). The processor 10A calculates the orientation of the smartphone 1 by integrating the angular velocity, acquired in step S103, once.

Examples of the orientation information of the smartphone 1 in step S103 when information on one circumference or more has been acquired are as illustrated in FIG. 7A and FIG. 7B. After calculating the contour of one circumference of the thigh cross-section in step S115, the processor 10A extracts the characteristic coefficients of the contour (step S217).

The processor 10A can take the orientation information and movement information at the time of a preset start action in FIG. 7A and FIG. 7B as the information at the start of measurement (time of 0 s). The preset start action may, for example, be the user pressing a start button. The orientation information and movement information when the smartphone 1 adopts a predetermined orientation may also be taken as the information at the start of measurement (time of 0 s). In other words, the smartphone 1 may be configured to set the time at which the inclination sensor detects that the back face 1B of the smartphone 1 is placed against the thigh as the time 0 and to calculate the contour of the thigh using data acquired from then on.

When determining that information has been acquired for less than one circumference in step S201, the processor 10A hides the thigh cross-sectional image (step S204) and terminates processing. Processing is terminated in order not to confuse the user by displaying data with insufficient accuracy.

After calculation of the contour in step S115, the smartphone 1 extracts the characteristic coefficients from the calculated contour (step S217). In this embodiment, the Fourier coefficients Sa1, Sa2, Sa3, and Sa4 that affect muscle area are extracted as the characteristic coefficients of the contour with the same method as in Embodiment 3.

The smartphone 1 estimates the user's muscle area in the thigh cross-section by substituting the characteristic coefficients extracted in step S217 into the muscle area estimation formula determined in advance (step S218). The muscle area estimation formula can be determined with the same method as the one illustrated in FIG. 22.

Next, on the basis of the muscle area estimated in step S218, the smartphone 1 selects the closest image to the user's thigh cross-section from among a plurality of thigh cross-sectional images stored in the storage 9 (step S119). The selected image is displayed on the display 2A of the smartphone 1 in the same way as in Embodiment 3 (step S110). In this way, in this embodiment, the muscle area of the thigh can be estimated.

Although movement information is obtained from the timer 11 in this embodiment, this configuration is not limiting. For example, the acceleration sensor 16 may be used as the second sensor as in Embodiment 1, and the movement amount of the smartphone 1 may be calculated by time integrating the acquired acceleration information twice.

In this embodiment, a sound is emitted at constant time intervals from the smartphone when the orientation information and the movement information are acquired. As a result, the user can easily move the smartphone at constant speed around the thigh.

According to this embodiment, the thigh cross-sectional image is hidden when measurement of the contour of the thigh is for less than one circumference. As a result, the user is not confused by a display of data with insufficient accuracy.

According to this embodiment, a partial contour of the thigh is calculated using orientation information and movement information starting when the smartphone 1 adopts a predetermined orientation. As a result, the smartphone 1 can always begin measuring from a constant, correct orientation.

In this embodiment, the shape characteristics are calculated from the contour when the subject flexes the thigh, but this disclosure is not limited to this case. For example, the shape characteristics may be calculated using the contours both for when the subject is and is not flexing the thigh. In this case, the muscle area estimation formula may be created by performing regression analysis with the coefficients representing the characteristics of both contours as independent variables and the muscle area, obtained by CT, as the dependent variable.

Figure 27A:
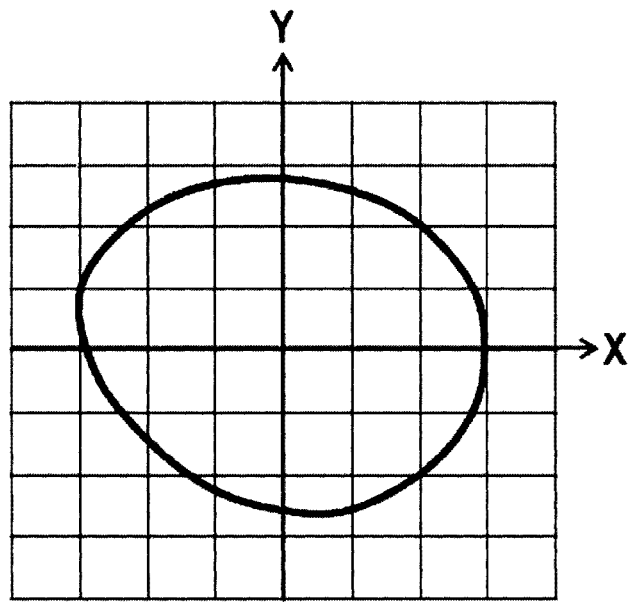
FIG. 27A is an example of the contour of the thigh for the same subject as calculated according to Embodiment 4.
Figure 27B:
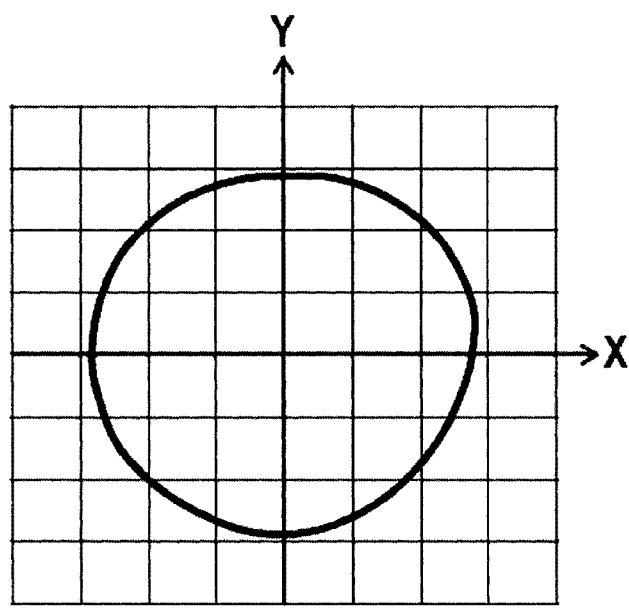
FIG. 27B is an example of the contour of the thigh for the same subject as calculated according to Embodiment 4.

FIGS. 27A and 27B illustrate an example of the contour of the right thigh for the same subject as calculated by the smartphone 1. FIG. 27A is an example of the contour when the thigh is not flexed, and FIG. 27B is an example of the contour when the thigh is flexed.

The contour of the thigh was measured while the subject was seated in a chair, with the foot placed horizontally on the ground. The contour in these figures is viewed from the right foot. The top of these figures indicates the front of the thigh, the bottom indicates the back of the thigh, the right side indicates the inner thigh, and the left side indicates the outer thigh. For example, when the thigh is not flexed (FIG. 27A), the contour of the thigh is an ellipse, with the outer back portion being nearly linear. For example, when the thigh is flexed (FIG. 27B), the contour of the thigh is nearly circular. In this way, by calculating the shape characteristics from two contours that differ in terms of flexing and estimating the muscle area, the estimation accuracy of the muscle area can be improved.

This disclosure is not limited to the above embodiments, and a variety of modifications and changes are possible. For example, it is possible for calculation and estimation to be made in only one state, flexed or relaxed.

Next, a system according to one of the embodiments of this disclosure is described in detail with reference to the accompanying drawings.

Figure 28:
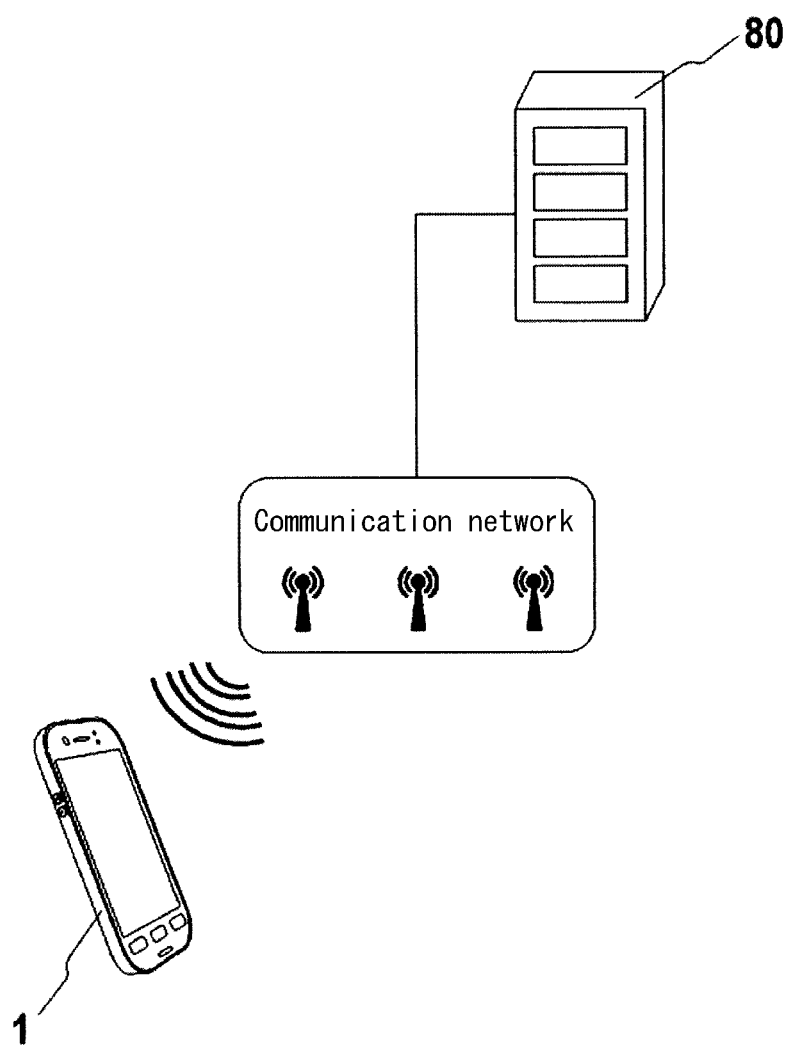
FIG. 28 conceptually illustrates a device and a system according to this disclosure, the device including a communication interface.

The system according to this embodiment in FIG. 28 includes a server 80, a smartphone 1, and a communication network. As illustrated in FIG. 28, the results of calculating the contour of the cross-section measured by the smartphone 1 are transmitted to the server 80 over the communication network. The server 80 classifies and determines the contour of the cross-section and transmits an image and advice to the user. The smartphone 1 can display the image and other information transmitted from the server 80 on the display 2A. By using a communication interface of the smartphone 1, information from a plurality of users can be collected on the server 80, thereby further improving the accuracy of classification and determination. A configuration may also be adopted to transmit the acquired orientation information, movement information, and circumferential length to the server 80. In this case, the server 80 calculates the contour of the cross-section. The burden of calculation on the controller 10 of the user's smartphone 1 can therefore be reduced, allowing the smartphone 1 to be reduced in size and simplified. The processing speed for calculation also improves.

As the system according to this embodiment, a configuration in which the smartphone 1 and the server 80 are connected over a communication network is illustrated. The system of this disclosure, however, is not limited to this configuration. It suffices for the system to include a measuring instrument that is moved along a human body, a first sensor configured to acquire orientation information of the measuring instrument, a device configured to obtain movement information of the measuring instrument, and a controller configured to calculate a contour of a cross-section of a human body. These components may be connected by a communication interface.

Characteristic embodiments have been described for a complete and clear disclosure. The appended claims, however, are not limited to the above embodiments and are to be understood as encompassing all of the possible modifications and alternate configurations that a person of ordinary skill in the art could make within the scope of the fundamental features indicated in this disclosure.

For example, in the above embodiments, the case of the smartphone 1 being the apparatus has been described, but the apparatus of this disclosure is not limited to the smartphone 1 and only needs to include at least the first sensor, the device, and the controller. Furthermore, the first sensor, the device, and the controller need not be provided inside the apparatus and may be individually separated.

In the above embodiments, the cases of estimating muscle area of the abdomen and the thigh have been described, but this disclosure may also be applied when measuring the contour of another cross-section.

In the above embodiments, the case of using a direction sensor and an angular velocity sensor as the first sensor has been described, but the first sensor may be any other component that can acquire orientation information of the apparatus. For example, an inclination sensor may be used as the first sensor.

The case of using an acceleration sensor or an electronic tape measure as the second sensor has been described, but the second sensor may be any other component that can acquire movement information of the apparatus. For example, an electronic roller distance meter that acquires movement information by detecting the number of revolutions of a wheel may be used as the second sensor.

In the above embodiments, examples of measuring the contour of a cross-section of a measured part over one circumference, a half circumference, and a ¼ circumference have been illustrated, but this disclosure is not limited to these examples. For example, the contour of the cross-section around the circumference may be measured twice and the data may be averaged to allow highly accurate measurement with little variation.

Much of the subject matter of this disclosure is described as a series of operations executed by a computer system and other hardware that can execute program instructions. Examples of the computer system and other hardware include a general-purpose computer, a Personal Computer (PC), a dedicated computer, a workstation, a Personal Communications System (PCS), a mobile (cellular) phone, a mobile phone with a data processing function, an RFID receiver, a game machine, an electronic notepad, a laptop computer, a Global Positioning System (GPS) receiver, and other programmable data processing apparatuses. It should be noted that in each embodiment, various operations are executed by a dedicated circuit (for example, individual logical gates interconnected in order to execute a particular function) implemented by program instructions (software), or by a logical block, program module, or the like executed by one or more processors. The one or more processors that execute a logical block, program module, or the like are, for example, one or more of a microprocessor, central processing unit (CPU), Application Specific Integrated Circuit (ASIC), Digital Signal Processor (DSP), Programmable Logic Device (PLD), Field Programmable Gate Array (FPGA), processor, controller, microcontroller, microprocessor, electronic device, other apparatus designed to be capable of executing the functions disclosed here, and/or a combination of any of the above. The disclosed embodiments are, for example, implemented by hardware, software, firmware, middleware, microcode, or a combination of any of these. The instructions may be program code or a code segment for executing the necessary tasks. The instructions may be stored on a machine-readable, non-transitory storage medium or other medium. The code segment may indicate a combination of any of the following: procedures, functions, subprograms, programs, routines, subroutines, modules, software packages, classes, instructions, data structures, or program statements. The code segment may transmit and/or receive information, data arguments, variables, or memory content to or from another code segment or hardware circuit in order for the code segment to connect to another code segment or hardware circuit.

The network used here may, unless indicated otherwise, be the Internet, an ad hoc network, a Local Area Network (LAN), a Wide Area Network (WAN), a Metropolitan Area Network (MAN), a cellular network, a Wireless Wide Area Network (WWAN), a Wireless Personal Area Network (WPAN), a Public Switched Telephone Network (PSTN), a Terrestrial Wireless Network, another network, or a combination of any of these. A wireless network for example includes constituent elements such as an access point (for example, a Wi-Fi access point) and a femtocell. Furthermore, a wireless communication device can connect to a wireless network that uses Wi-Fi, Bluetooth®, cellular communication technology (such as Code Division Multiple Access (CDMA), Time Division Multiple Access (TDMA), Frequency Division Multiple Access (FDMA), Orthogonal Frequency Division Multiple Access (OFDMA), or Single-Carrier Frequency Division Multiple Access (SC-FDMA)), or other wireless technology and/or technical standards. One or more techniques may be adopted for the networks. Such techniques for example include Universal Mobile Telecommunications System (UTMS), Long Term Evolution (LTE), Evolution-Data Optimized or Evolution-Data Only (EV-DO), GSM®, Worldwide Interoperability for Microwave Access (WiMAX), Code Division Multiple Access-2000 (CDMA-2000), or Time Division Synchronous Code Division Multiple Access (TD-SCDMA).

The circuit configuration of the communication interface or other such components provides functionality by using a variety of wireless communication networks, such as WWAN, WLAN, and WPAN. The WWAN may be a network such as a CDMA network, a TDMA network, an FDMA network, an OFDMA network, or a SC-FDMA network. The CDMA network implements one or more Radio Access Technologies (RAT), such as CDMA2000 and Wideband-CDMA (W-CDMA). CDMA2000 includes the IS-95, IS-2000, and IS-856 standards. The TDMA network can implement GSM®, Digital Advanced Phone System (D-AMPS), and other RATs. GSM® and W-CDMA are listed in documents issued by the consortium known as 3rd Generation Partnership Project (3GPP). CDMA2000 is listed in documents issued by the consortium known as 3rd Generation Partnership Project 2 (3GPP2). The WLAN may be an IEEE802.11x network. The WPAN may be a Bluetooth® network, an IEEE802.15x network, or other type of network. CDMA may be implemented as a wireless technique such as Universal Terrestrial Radio Access (UTRA) or CDMA2000. TDMA may be implemented by a wireless technique such as GSM®/General Packet Radio Service (GPRS)/Enhanced Data Rates for GSM® (EDGE). OFDMA may be implemented by wireless techniques such as Institute of Electrical and Electronics Engineers (IEEE) 802.11 (Wi-Fi), IEEE802.16 (WiMAX), IEEE802.20, or Evolved UTRA (E-UTRA). These techniques may be used in a combination of any of WWAN, WLAN, and/or WPAN. These techniques may also be implemented in order to use an Ultra Mobile Broadband (UMB) network, a High Rate Packet Data (HRPD) network, a CDMA20001X network, GSM®, Long-Term Evolution (LTE), or the like.

The storage used here may also be configured by a computer-readable, tangible carrier (medium) in the categories of solid-state memory, magnetic disks, and optical discs. Data structures and an appropriate set of computer instructions, such as program modules, for causing a processor to execute the techniques disclosed herein are stored on these media. Examples of computer-readable media include an electrical connection with one or more wires, a magnetic disk storage medium, a magnetic cassette, a magnetic tape, or other magnetic or optical storage medium (such as a Compact Disc (CD), laser Disc®, DVD®, Floppy® disk, and Blu-ray® Disc (laser disc and floppy are registered trademarks in Japan, other countries, or both)), portable computer disk, Random Access Memory (RAM), Read-Only Memory (ROM), rewritable programmable ROM such as EPROM, EEPROM, or flash memory, another tangible storage medium that can store information, or a combination of any of these. The memory may be provided internal and/or external to a processor/processing unit. As used in this disclosure, the term "memory" refers to all types of long-term storage, short-term storage, volatile, non-volatile, or other memory. No limitation is placed on the particular type or number of memories, or on the type of medium for memory storage.

While the disclosed system has a variety of modules and/or units for implementing particular functions, these modules and units have only been indicated schematically in order to briefly illustrate the functionality thereof. It should be noted that no particular hardware and/or software is necessarily indicated. In this sense, it suffices for the modules, units, and other constituent elements to be hardware and/or software implemented so as to substantially execute the particular functions described here. The various functions or different constituent elements may be combined with or separated from hardware and/or software in any way, and each may be used individually or in some combination. An input/output (I/O) device or user interface including, but not limited to, a keyboard, display, touchscreen, or pointing device may be connected to the system directly or via an I/O controller. In this way, the various subject matter disclosed herein may be embodied in a variety of forms, and all such embodiments are included in the scope of the subject matter in this disclosure.

The invention claimed is:

1. A system for estimating muscle area, the system comprising:
a measuring instrument comprising a first sensor configured to acquire orientation information of the measuring instrument and a device configured to obtain movement information of the measuring instrument; and
a controller configured to estimate muscle area in a cross-section of a human body on a basis of shape characteristics calculated from an at least partial contour of the human body, the at least partial contour being calculated on a basis of the orientation information and the movement information.

2. The system of claim 1, wherein the controller displays, on a display, an image corresponding to the estimated muscle area.

3. The system of claim 2, further comprising:
a memory configured to store a plurality of CT sample images;
wherein the controller displays, on the display, a CT sample image from among the plurality of CT sample images, the CT sample image at least corresponding to the estimated muscle area.

4. An apparatus comprising:
a first sensor configured to acquire orientation information of the apparatus;
a device configured to obtain movement information of the apparatus; and
a controller configured to estimate muscle area in a cross-section of a human body on a basis of shape characteristics calculated from an at least partial contour of the human body, the at least partial contour being calculated on a basis of the orientation information and the movement information.

5. The apparatus of claim 4, further comprising a display, an image corresponding to the estimated muscle area being displayed on the display.

6. The apparatus of claim 5, further comprising:
a memory configured to store a plurality of CT sample images;
wherein the controller displays, on the display, a CT sample image from among the plurality of CT sample images, the CT sample image at least corresponding to the estimated muscle area.

7. The apparatus of claim 4, wherein the first sensor comprises at least one of a direction sensor, an angular velocity sensor, and an inclination sensor.

8. The apparatus of claim 4, wherein the device comprises a second sensor configured to obtain movement information of the apparatus.

9. The apparatus of claim 8, wherein the second sensor comprises at least one of an acceleration sensor and an electronic tape measure.

10. The apparatus of claim 4, wherein the device comprises a timer.

11. A method for estimating muscle area comprising:
obtaining orientation information and movement information of an apparatus; and
with a controller,
calculating an at least partial contour of a human body on a basis of the orientation information and the movement information;
calculating shape characteristics from the calculated at least partial contour of the human body; and
estimating muscle area in a cross-section of the human body on a basis of the shape characteristics.

* * * * *